United States Patent [19]

Levitt

[11] 4,378,991

[45] Apr. 5, 1983

[54] HERBICIDAL O-ARYL OR ALKARYLSULFONYLUREAS

[75] Inventor: George Levitt, Wilmington, Del.

[73] Assignee: E. I. Du Pont de Nemours and Company, Wilmington, Del.

[21] Appl. No.: 264,331

[22] Filed: May 26, 1981

Related U.S. Application Data

[63] Continuation-in-part of Ser. No. 168,347, Jul. 11, 1980, abandoned.

[51] Int. Cl.³ .................. C07D 251/46; C07D 251/16; C07D 251/22; A01N 43/66
[52] U.S. Cl. .......................................... 71/93; 544/211
[58] Field of Search ............................ 544/211; 71/93

[56] References Cited

U.S. PATENT DOCUMENTS

| | | | |
|---|---|---|---|
| 4,127,405 | 11/1978 | Levitt | 544/211 |
| 4,225,337 | 9/1980 | Levitt | 544/211 |
| 4,238,621 | 12/1980 | Levitt | 544/211 |
| 4,257,802 | 3/1981 | Levitt | 544/211 |
| 4,301,286 | 11/1981 | Schwing | 544/211 |
| 4,302,241 | 11/1981 | Levitt | 544/211 |
| 4,310,346 | 1/1982 | Levitt et al. | 544/211 |
| 4,332,611 | 6/1982 | Petersen | 544/211 |

*Primary Examiner*—John M. Ford

[57] ABSTRACT

N-(heterocyclicaminocarbonyl)-o-(aryl or alkaryl)benzenesulfonamides, such as N-[(4,6-dimethoxy-1,3,5-triazin-2-yl)aminocarbonyl]-[1,1'-biphenyl]-2-sulfonamide are useful as preemergent or postemergent herbicides or as plant growth regulants.

27 Claims, No Drawings

HERBICIDAL O-ARYL OR ALKARYLSULFONYLUREAS

CROSS-REFERENCE TO RELATED APPLICATIONS

This application is a continuation-in-part of U.S. Ser. No. 168,347, filed July 11, 1980, (now abandoned).

BACKGROUND OF THE INVENTION

This invention relates to novel N-(heterocyclicaminocarbonyl)-o-(hydrocarbyl) benzenesulfonamides which are useful as agricultural chemicals and in particular as herbicides and growth regulants.

Netherlands Pat. No. 121,788, published Sept. 15, 1966, teaches the preparation of compounds of Formula (I) and their use as general or selective herbicides:

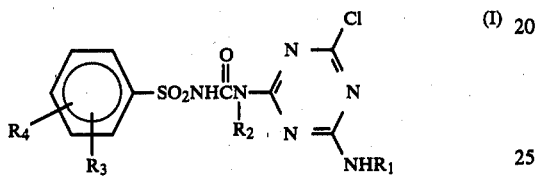

wherein $R_1$ and $R_2$ may independently be alkyl of 1–4 carbon atoms; and $R_3$ and $R_4$ may independently be hydrogen, chlorine or alkyl of 1–4 carbon atoms.

Compounds of Formula (II), and their use as antidiabetic agents, are reported in *J. Drug. Res.* 6, 123 (1974):

wherein R is pyridyl.

In U.S. Pat. No. 4,127,405, compounds are disclosed of the general formula:

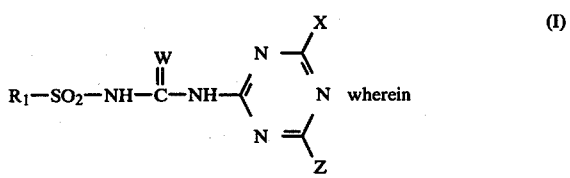

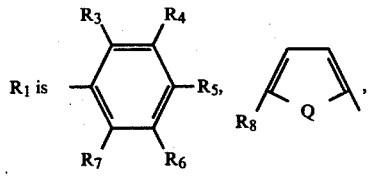

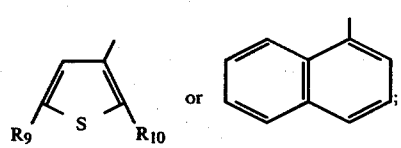

$R_3$ and $R_6$ are independently hydrogen, fluorine, chlorine, bromine, iodine, alkyl of 1–4 carbon atoms, alkoxy of 1–4 carbon atoms, nitro, trifluoromethyl, cyano, $CH_3S(O)_n-$ or $CH_3CH_2S(O)_n-$;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or alkoxy of 1–2 carbon atoms;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S-$ or $CH_3OCH_2-$; and Z is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In particular, the patent discloses orthosubstituted compounds wherein the substitution is $C_1$–$C_4$ alkyl.

The presence of undesired vegetation causes substantial damage to useful crops, especially agricultural products that satisfy man's basic food needs, such as soybeans, corn, wheat and the like. The current population explosion and concomitant world food shortage demand improvements in the efficiency of producing these crops. Preventing or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. However, the need exists for still more effective herbicides that destroy or retard weeds without causing significant damage to useful crops.

SUMMARY OF THE INVENTION

This invention relates to novel compounds of Formula I, suitable agricultural compositions containing them, and their method of use as general, as well as, selective herbicides.

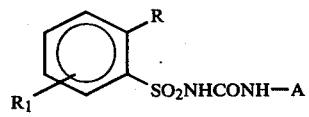

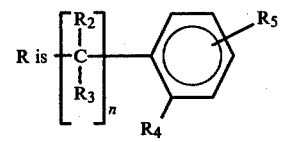

n is 0 or 1;

$R_1$ is H, F, Cl, Br, $NO_2$, $CF_3$, $C_1$–$C_4$ alkyl, $OCF_3$ or $C_1$–$C_4$ alkoxy;

$R_2$ and $R_3$ are selected independently from H and $CH_3$;

$R_4$ is H, $C_1$–$C_3$ alkyl, F, Cl, Br, $CF_3$, $OCF_3$ or $C_1$–$C_3$ alkoxy;

$R_5$ is $CH_3$, Cl, Br or H;

A is

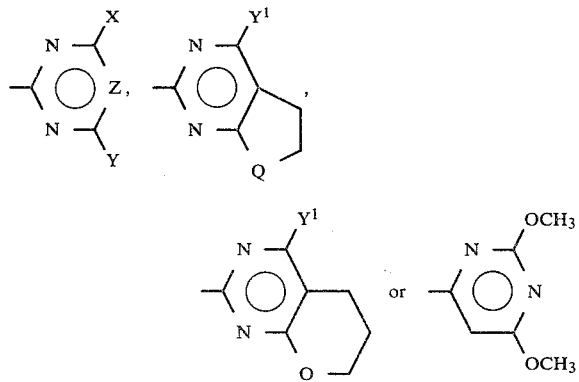

X is H, $CH_3$, $OCH_3$, $OCH_2CH_3$, $OCH_2CF_3$, $CH_2OCH_3$ or Cl;

Y is $CH_3$, $OCH_3$ or $OCH_2CH_3$;

Z is N, CH, CCl, C-Br, C-CN, $CCH_3$, $C-CH_2CH_3$, $C-CH_2CH_2Cl$ or $C-CH_2CH=CH_2$;

$Y^1$ is H, $CH_3$, $OCH_3$ or Cl; and

Q is $CH_2$ or O;

provided that the total number of carbons in R is less than or equal to nine.

PREFERRED COMPOUNDS

Preferred for reasons of higher herbicidal activity and/or more favorable ease of synthesis are:

(1) Compounds of Formula I in which n is 0;

(2) Compounds of Preferred 1 in which A is

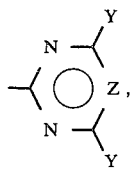

X is $CH_3$, $OCH_3$, $OCH_2CH_3$ or $CH_2OCH_3$;

Y is $CH_3$ or $OCH_3$; and

Z is CH or N.

(3) Compounds of Preferred 2 in which $R_5$ is H, and $R_4$ is H or Cl.

(4) Compounds of Preferred 3 in which $R_1$ is H or Cl.

Specifically preferred for highest herbicidal activity and/or most favorable ease of synthesis are:

3,2'-dichloro-N-[(4-methoxy-6-methyl-1,3,5-triazin-2-yl)aminocarbonyl][1,1'-biphenyl]-2-sulfonamide;

N-[(4,6-dimethylpyrimidin-2-yl)aminocarbonyl][1,1'-biphenyl]-2-sulfonamide;

N-[(4,6-dimethoxypyrimidin-2-yl)aminocarbonyl][1,1'-biphenyl]-2-sulfonamide;

N-[(4-methoxy-6-methylpyrimidin-2-yl)aminocarbonyl][1,1'-biphenyl]-2-sulfonamide;

N-[(4,6-dimethyl-1,3,5-triazin-2-yl)aminocarbonyl][1,1'-biphenyl]-2-sulfonamide;

N-[(4,6-dimethoxy-1,3,5-triazin-2-yl)aminocarbonyl][1,1'-biphenyl]-2-sulfonamide;

N-[(4-methoxy-6-methyl-1,3,5-triazin-2-yl)aminocarbonyl][1,1'-biphenyl]-2-sulfonamide;

DETAILED DESCRIPTION OF THE INVENTION

The compounds of Formula I can be made by the reaction sequence:

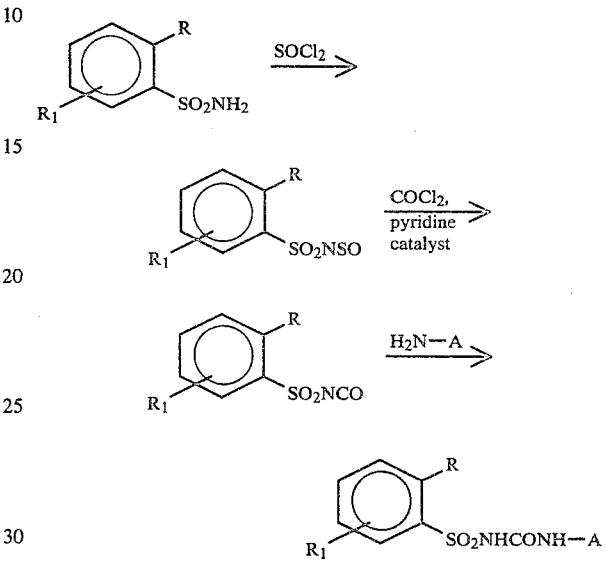

Sulfonyl isocyanates can be made, for example, by the method of Ulrich et al., [J. Org. Chem. 34, 3200 (1969)]. The sulfonamide is boiled under reflux with an excess of thionyl chloride, which functions as a reactant and solvent. The reaction is continued until the sulfonamide protons are undetectable in the proton resonance spectrum. An overnight reaction period (about 16 hours) is generally sufficient. The thionyl chloride is evaporated and the residue dissolved in an inert solvent (such as toluene, benzene, xylene, etc.), contacted with a catalytic amount of pyridine, then with at least one equivalent of phosgene. The mixture is heated to about 60°–140°, with 80°–100° preferred. Conversion to the isocyanate is substantially complete within about ¼ to 3 hours. The mixture containing the sulfonyl isocyanate can be used directly for the next reaction step (formation of sulfonylurea) or the sulfonyl isocyanate can be isolated by filtration and evaporation of the solvent. The isocyanate can be redissolved in a suitable solvent (e.g., methylene chloride, benzene, toluene, xylene or acetonitrile, etc.) and the solution contacted with the aminoheterocycle $H_2N$—A to provide the sulfonylurea product. The reaction is generally exothermic. Conveniently, the starting reaction temperature is ambient, but can be varied from about 0° to 100° if desired. The product can be isolated by filtration if it precipitates from the reaction mixture; otherwise, the solvent can be evaporated and the residual product obtained thereby, with optional further purification obtained by trituration with an organic solvent (e.g., diethyl ether, 1-chlorobutane, etc.) in which it is only sparingly soluble.

Exemplary compounds of structure I are listed below:

TABLE I

[Structure: phenyl ring with R (position 2) and R₁ (positions 3-6 numbered), connected via SO₂NHCNH-C(=O) to a pyrimidine ring with two CH₃ groups]

| R₁ | R | m.p. °C. |
|---|---|---|
| H | phenyl | 78° (dec.) |
| 6-F | 2-F-phenyl | |
| 6-Cl | 2-Cl-phenyl | |
| 6-Br | 2-Br-phenyl | |
| 4-NO₂ | 2-Cl-phenyl | |
| 6-CF₃ | 2-CF₃-phenyl | |
| 6-CH₃ | 2-CH₃-phenyl | |
| 4-CH₃(CH₂)₃ | 2-Cl-phenyl | |
| 6-CF₃O | 2-OCF₃-phenyl | |
| 6-CH₃O | 2-OCH₃-phenyl | |
| 4-CH₃(CH₂)₃O | 2-Cl-phenyl | |
| H | 3-Cl-4-methylphenyl | |
| H | 3-Cl-4-methylphenyl | |
| H | 2-C₂H₅-phenyl | |
| H | 2-CH₂CH₂CH₃-phenyl | |
| H | 2-CH(CH₃)₂-phenyl | |
| 3-Cl | phenyl | |
| 4-Cl | phenyl | |
| 5-Cl | phenyl | |
| H | 4-Br-phenyl | |
| H | 4-CH₃-phenyl | |
| H | 3,4-diCl-phenyl | |
| H | benzyl (phenyl-CH₂) | |
| H | 2-CH₃-benzyl | |
| H | 2-C₂H₅-benzyl | |
| H | 2-F-benzyl | |
| 6-CH₃(CH₂)₂O | 2-O(CH₂)₂CH₃-phenyl | |
| H | 2-Cl-benzyl | |
| H | 2-Br-benzyl | |
| H | 4-CH₃-benzyl | |
| H | 4-Cl-benzyl | |
| H | 4-Br-benzyl | |
| H | 3,2-diCl-benzyl | |

TABLE I-continued
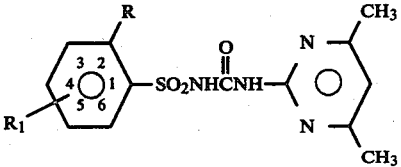
| R₁ | R | m.p. °C |
|---|---|---|
| H |  | |
| H | 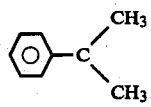 | |
TABLE II
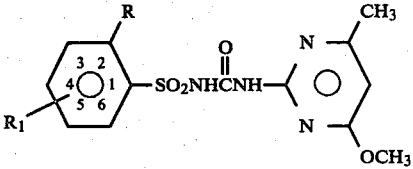
| R₁ | R | m.p. °C |
|---|---|---|
| H |  | 128–130 |
| 6-F |  | |
| 6-Cl |  | |
| 6-Br |  | |
| 4-NO₂ |  | |
| 6-CF₃ |  | |
| 6-CH₃ |  | |
| 4-CH₃(CH₂)₃ |  | |
| 6-CF₃O |  | |
| 6-CH₃O |  | |
| 4-CH₃(CH₂)₃O |  | |
TABLE II-continued
| R₁ | R | m.p. °C |
|---|---|---|
| H |  | |
| H |  | |
| H |  | |
| H |  | |
| H |  | |
| 3-Cl |  | |
| 4-Cl |  | |
| 5-Cl |  | |
| H |  | |
| H |  | |
| H |  | |
| H |  | |
| H |  | |
| H | | |
| 6-CH₃(CH₂)₂O |  | |

TABLE II-continued

Structure: Ar(R,R₁)-SO₂NHC(=O)NH-pyrimidine with 4-CH₃, 6-OCH₃ substituents (positions 3,2,4,1,5,6 on phenyl ring)

| R₁ | R | m.p. °C. |
|---|---|---|
| H | 2-CH₂(C₆H₄)-Cl (o-chlorobenzyl) | |
| H | 2-CH₂(C₆H₄)-Br (o-bromobenzyl) | |
| H | 4-CH₃-C₆H₄-CH₂ | |
| H | 4-Cl-C₆H₄-CH₂ | |
| H | 4-Br-C₆H₄-CH₂ | |
| H | 2,4-diCl-C₆H₃-CH₂ | |
| H | C₆H₅-CH(CH₃) | |
| H | C₆H₅-C(CH₃)₂ | |

TABLE III

Structure: Ar(R,R₁)-SO₂NHC(=O)NH-pyrimidine with 4-OCH₃, 6-OCH₃ substituents

| R₁ | R | m.p. °C. |
|---|---|---|
| H | C₆H₅ | 215–216 |
| 6-F | 2-F-C₆H₄ | |
| 6-Cl | 2-Cl-C₆H₄ | |
| 6-Br | 2-Br-C₆H₄ | |
| 4-NO₂ | 2-Cl-C₆H₄ | |

TABLE III-continued

| R₁ | R | m.p. °C. |
|---|---|---|
| 6-CF₃ | 2-CF₃-C₆H₄ | |
| 6-CH₃ | 2-CH₃-C₆H₄ | |
| 4-CH₃(CH₂)₃ | 2-Cl-C₆H₄ | |
| 6-CF₃O | 2-OCF₃-C₆H₄ | |
| 6-CH₃O | 2-OCH₃-C₆H₄ | |
| 4-CH₃(CH₂)₃O | 2-Cl-C₆H₄ | |
| H | 2-Cl-C₆H₄ | |
| H | 4-Cl-C₆H₄ | |
| H | 2-C₂H₅-C₆H₄ | |
| H | 2-CH₂CH₂CH₃-C₆H₄ | |
| H | 2-CH(CH₃)₂-C₆H₄ | |
| 3-Cl | C₆H₅ | |
| 4-Cl | C₆H₅ | |
| 5-Cl | C₆H₅ | |
| H | 4-Br-C₆H₄ | |
| H | 4-CH₃-C₆H₄ | |
| H | 2,4-diCl-C₆H₃ | |

TABLE III-continued

Structure: R-substituted phenyl (positions 3,2 / 4,1 / 5,6 with R at top and R₁ at bottom) — SO₂NHCNH — pyrimidine ring with OCH₃ at 4 and 6 positions, N at 1,3, and C=O on the urea linkage.

| R₁ | R | m.p. °C. |
|---|---|---|
| H | C₆H₅—CH₂— (benzyl) | |
| H | 2-CH₃—C₆H₄—CH₂— | |
| H | 2-C₂H₅—C₆H₄—CH₂— | |
| H | 2-F—C₆H₄—CH₂— | |
| 6-CH₃(CH₂)₂O | 2-CH₃(CH₂)₂O—C₆H₄— | |
| H | 2-Cl—C₆H₄—CH₂— | |
| H | 2-Br—C₆H₄—CH₂— | |
| H | 4-CH₃—C₆H₄—CH₂— | |
| H | 4-Cl—C₆H₄—CH₂— | |
| H | 4-Br—C₆H₄—CH₂— | |
| H | 2,4-Cl₂—C₆H₃—CH₂— | |
| H | C₆H₅—CH(CH₃)— | |
| H | C₆H₅—C(CH₃)₂— | |

TABLE IV

Structure: R-substituted phenyl — SO₂NHCNH — pyrimidine ring with CH₃ at 4 and 6 positions, N at 1,3, and C=O on the urea linkage.

| R₁ | R |
|---|---|
| H | C₆H₅— |
| 6-F | 2-F—C₆H₄— |
| 6-Cl | 2-Cl—C₆H₄— |
| 6-Br | 2-Br—C₆H₄— |
| 4-NO₂ | 2-Cl—C₆H₄— |
| 6-CF₃ | 2-CF₃—C₆H₄— |
| 6-CH₃ | 2-CH₃—C₆H₄— |
| 4-CH₃(CH₂)₃ | 2-Cl—C₆H₄— |
| 6-CF₃O | 2-CF₃O—C₆H₄— |
| 6-CH₃O | 2-CH₃O—C₆H₄— |
| 4-CH₃(CH₂)₃O | 2-Cl—C₆H₄— |
| H | 2-Cl,5-CH₃—C₆H₃— |
| H | 4-Cl—C₆H₄— |
| H | 2-C₂H₅—C₆H₄— |
| H | 2-CH₂CH₂CH₃—C₆H₄— |
| H | 2-CH(CH₃)₂—C₆H₄— |
| 3-Cl | C₆H₅— |

TABLE IV-continued

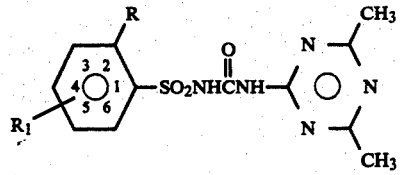

| R₁ | R |
|---|---|
| 4-Cl | phenyl |
| 5-Cl | phenyl |
| H | 4-Br-phenyl |
| H | 4-CH₃-phenyl |
| H | 2,4-diCl-phenyl |
| H | benzyl (PhCH₂) |
| H | 2-CH₃-benzyl |
| H | 2-C₂H₅-benzyl |
| H | 2-F-benzyl |
| 6-CH₃(CH₂)₂O | 2-O(CH₂)₂CH₃-benzyl |
| H | 2-Cl-benzyl |
| H | 2-Br-benzyl |
| H | 4-CH₃-benzyl |
| H | 4-Cl-benzyl |
| H | 4-Br-benzyl |
| H | 3,4-diCl-benzyl |

TABLE IV-continued

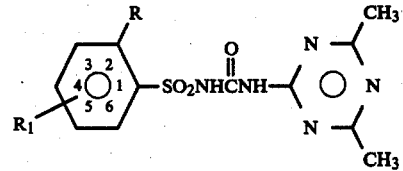

| R₁ | R |
|---|---|
| H | PhCH(CH₃)- |
| H | PhC(CH₃)₂- |

TABLE V

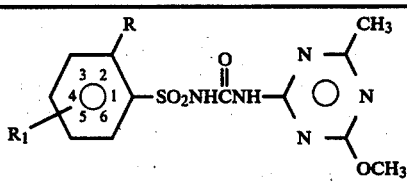

| R₁ | R | m.p. °C. |
|---|---|---|
| H | phenyl | |
| 6-F | 2-F-phenyl | |
| 6-Cl | 2-Cl-phenyl | 141° (dec) |
| 6-Br | 2-Br-phenyl | |
| 4-NO₂ | 2-Cl-phenyl | |
| 6-CF₃ | 2-CF₃-phenyl | |
| 6-CH₃ | 2-CH₃-phenyl | |
| 4-CH₃(CH₂)₃ | 2-Cl-phenyl | |
| 6-CF₃O | 2-OCF₃-phenyl | |
| 6-CH₃O | 2-OCH₃-phenyl | |
| 4-CH₃(CH₂)₃O | 2-Cl-phenyl | |

TABLE V-continued

[Structure: R-substituted phenyl-SO$_2$NHCNH-triazine with CH$_3$ and OCH$_3$ groups]

| R$_1$ | R | m.p. °C. |
|---|---|---|
| H | 3-Cl-phenyl (as shown: phenyl with Cl) | |
| H | 4-Cl-phenyl | |
| H | 2-C$_2$H$_5$-phenyl | |
| H | 2-CH$_2$CH$_2$CH$_3$-phenyl | |
| H | 2-CH(CH$_3$)$_2$-phenyl | |
| 3-Cl | phenyl | |
| 4-Cl | phenyl | |
| 5-Cl | phenyl | |
| H | 4-Br-phenyl | |
| H | 4-CH$_3$-phenyl | |
| H | 2,4-Cl$_2$-phenyl | |
| H | phenyl-CH$_2$ | |
| H | 2-CH$_3$-phenyl-CH$_2$ | |
| H | 2-C$_2$H$_5$-phenyl-CH$_2$ | |
| H | 2-F-phenyl-CH$_2$ | |
| 6-CH$_3$(CH$_2$)$_2$O | 2-O(CH$_2$)$_2$CH$_3$-phenyl | |

TABLE V-continued

[Same structure as above]

| R$_1$ | R | m.p. °C. |
|---|---|---|
| H | 2-Cl-phenyl-CH$_2$ | |
| H | 2-Br-phenyl-CH$_2$ | |
| H | 4-CH$_3$-phenyl-CH$_2$ | |
| H | 4-Cl-phenyl-CH$_2$ | |
| H | 4-Br-phenyl-CH$_2$ | |
| H | 3,4-Cl$_2$-phenyl-CH$_2$ | |
| H | phenyl-CH(CH$_3$) | |
| H | phenyl-C(CH$_3$)$_2$ | |

TABLE VI

[Structure: R-substituted phenyl-SO$_2$NHCNH-triazine with two OCH$_3$ groups]

| R$_1$ | R | m.p. °C. |
|---|---|---|
| H | phenyl | 167–172 |
| 6-F | 2-F-phenyl | |
| 6-Cl | 2-Cl-phenyl | |
| 6-Br | 2-Br-phenyl | |
| 4-NO$_2$ | 2-Cl-phenyl | |

TABLE VI-continued

Structure: R-substituted phenyl-SO₂NHCNH-C(=O)-[triazine with two OCH₃ groups]

| R₁ | R | m.p. °C. |
|---|---|---|
| 6-CF₃ | 2-CF₃-phenyl | |
| 6-CH₃ | 2-CH₃-phenyl | |
| 4-CH₃(CH₂)₃ | 2-Cl-phenyl | |
| 6-CF₃O | 2-OCF₃-phenyl | |
| 6-CH₃O | 2-OCH₃-phenyl | |
| 4-CH₃(CH₂)₃O | 2-Cl-phenyl | |
| H | 3-Cl-phenyl | |
| H | 4-Cl-phenyl | |
| H | 2-C₂H₅-phenyl | |
| H | 2-CH₂CH₂CH₃-phenyl | |
| H | 2-CH(CH₃)₂-phenyl | |
| 3-Cl | phenyl | |
| 4-Cl | phenyl | |
| 5-Cl | phenyl | |
| H | 4-Br-phenyl | |
| H | 4-CH₃-phenyl | |
| H | 3,4-diCl-phenyl | |

| R₁ | R | m.p. °C. |
|---|---|---|
| H | benzyl (C₆H₅CH₂) | |
| H | 2-CH₃-benzyl | |
| H | 2-C₂H₅-benzyl | |
| H | 2-F-benzyl | |
| 6-CH₃(CH₂)₂O | 2-O(CH₂)₂CH₃-phenyl | |
| H | 2-Cl-benzyl | |
| H | 2-Br-benzyl | |
| H | 4-CH₃-benzyl | |
| H | 4-Cl-benzyl | |
| H | 4-Br-benzyl | |
| H | 3,4-diCl-benzyl | |
| H | α-methylbenzyl (C₆H₅CH(CH₃)) | |
| H | α,α-dimethylbenzyl (C₆H₅C(CH₃)₂) | |

TABLE VII

| $R_1$ | R |
|---|---|
| H | phenyl |
| 6-F | 2-F-phenyl |
| 6-Cl | 2-Cl-phenyl |
| 6-Br | 2-Br-phenyl |
| 4-NO$_2$ | 2-Cl-phenyl |
| 6-CF$_3$ | 2-CF$_3$-phenyl |
| 6-CH$_3$ | 2-CH$_3$-phenyl |
| 4-CH$_3$(CH$_2$)$_3$ | 2-Cl-phenyl |
| 6-CF$_3$O | 2-OCF$_3$-phenyl |
| 6-CH$_3$O | 2-OCH$_3$-phenyl |
| 4-CH$_3$(CH$_2$)$_3$O | 2-Cl-phenyl |
| H | 3-Cl-phenyl |
| H | 4-Cl-phenyl |
| H | 2-C$_2$H$_5$-phenyl |
| H | 2-CH$_2$CH$_2$CH$_3$-phenyl |
| H | 2-CH(CH$_3$)$_2$-phenyl |
| 3-Cl | phenyl |
| 4-Cl | phenyl |
| 5-Cl | phenyl |
| H | 4-Br-phenyl |
| H | 4-CH$_3$-phenyl |
| H | 3,4-Cl$_2$-phenyl |
| H | benzyl |
| H | 2-CH$_3$-benzyl |
| H | 2-C$_2$H$_5$-benzyl |
| H | 2-F-benzyl |
| 6-CH$_3$(CH$_2$)$_2$O | 2-O(CH$_2$)$_2$CH$_3$-phenyl |
| H | 2-Cl-benzyl |
| H | 2-Br-benzyl |
| H | 4-CH$_3$-benzyl |
| H | 4-Cl-benzyl |
| H | 4-Br-benzyl |
| H | 3,4-Cl$_2$-benzyl |

Structure header (top of table):

Aryl(R, R$_1$-substituted)—SO$_2$NHCNH—pyrimidine(OC$_2$H$_5$, CH$_3$)
with C=O in urea linkage.

TABLE VII-continued

Structure: R-substituted phenyl-SO₂NHCNH-pyrimidine with OC₂H₅ and CH₃ substituents

| R₁ | R |
|---|---|
| H | phenyl-CH(CH₃) |
| H | phenyl-C(CH₃)₂ |

TABLE VIII

Structure: R-substituted phenyl-SO₂NHCNH-pyrimidine with OCH₂CF₃ and CH₃ substituents

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |

TABLE VIII-continued

Structure: R-substituted phenyl-SO₂NHCNH-pyrimidine with OCH₂CF₃ and CH₃ substituents

| R₁ | R |
|---|---|
| H | 3-Cl-phenyl |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |
| 4-Cl | phenyl |
| 5-Cl | phenyl |
| H | 4-Br-phenyl |
| H | 4-CH₃-phenyl |
| H | 2,3-Cl₂-phenyl |
| H | phenyl-CH₂ |
| H | 2-CH₃-phenyl-CH₂ |
| H | 2-C₂H₅-phenyl-CH₂ |
| H | 2-F-phenyl-CH₂ |
| 6-CH₃(CH₂)₂O | 2-O(CH₂)₂CH₃-phenyl |

TABLE VIII-continued

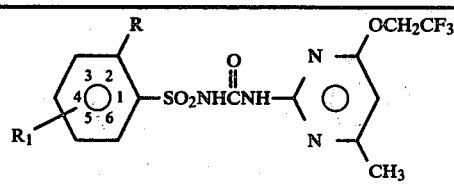

| R₁ | R |
|---|---|
| H | 2-Cl-benzyl (o-ClC₆H₄CH₂) |
| H | 2-Br-benzyl |
| H | 4-CH₃-benzyl |
| H | 4-Cl-benzyl |
| H | 4-Br-benzyl |
| H | 2,4-Cl₂-benzyl |
| H | C₆H₅CH(CH₃)– |
| H | C₆H₅C(CH₃)₂– |

TABLE IX

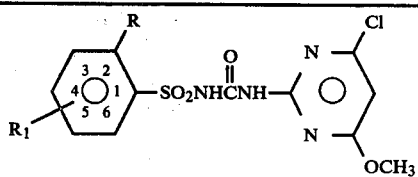

| R₁ | R |
|---|---|
| H | C₆H₅ |
| 6-F | 2-F-C₆H₄ |
| 6-Cl | 2-Cl-C₆H₄ |
| 6-Br | 2-Br-C₆H₄ |
| 4-NO₂ | 2-Cl-C₆H₄ |

TABLE IX-continued

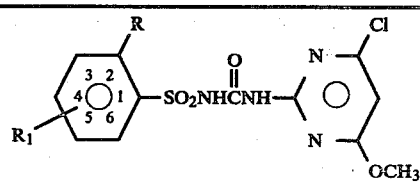

| R₁ | R |
|---|---|
| 6-CF₃ | 2-CF₃-C₆H₄ |
| 6-CH₃ | 2-CH₃-C₆H₄ |
| 4-CH₃(CH₂)₃ | 2-Cl-C₆H₄ |
| 6-CF₃O | 2-OCF₃-C₆H₄ |
| 6-CH₃O | 2-OCH₃-C₆H₄ |
| 4-CH₃(CH₂)₃O | 2-Cl-C₆H₄ |
| H | 3-Cl-2-CH₃-C₆H₃ |
| H | 4-Cl-C₆H₄ |
| H | 2-C₂H₅-C₆H₄ |
| H | 2-CH₂CH₂CH₃-C₆H₄ |
| H | 2-CH(CH₃)₂-C₆H₄ |
| 3-Cl | C₆H₅ |
| 4-Cl | C₆H₅ |
| 5-Cl | C₆H₅ |
| H | 4-Br-C₆H₄ |
| H | 4-CH₃-C₆H₄ |
| H | 3,4-Cl₂-C₆H₃ |

TABLE IX-continued

Structure: Phenyl ring (with R at position 2, R₁ at position 5) — SO₂NHC(O)NH — pyrimidine ring (with Cl, OCH₃, N's)

| R₁ | R |
|---|---|
| H | C₆H₅—CH₂— |
| H | 2-CH₃-C₆H₄—CH₂— |
| H | 2-C₂H₅-C₆H₄—CH₂— |
| H | 2-F-C₆H₄—CH₂— |
| 6-CH₃(CH₂)₂O | 2-CH₃-C₆H₄—O(CH₂)₂CH₃ |
| H | 2-Cl-C₆H₄—CH₂— |
| H | 2-Br-C₆H₄—CH₂— |
| H | 4-CH₃-C₆H₄—CH₂— |
| H | 4-Cl-C₆H₄—CH₂— |
| H | 4-Br-C₆H₄—CH₂— |
| H | 2,4-Cl₂-C₆H₃—CH₂— |
| H | C₆H₅—CH(CH₃)— |
| H | C₆H₅—C(CH₃)₂— |

TABLE X

Structure: Phenyl ring (with R at position 2, R₁ at position 5) — SO₂NHC(O)NH — pyrimidine ring (with CH₃, Cl, CH₃, N's)

| R₁ | R |
|---|---|
| H | C₆H₅— |
| 6-F | 2-F-C₆H₄— |
| 6-Cl | 2-Cl-C₆H₄— |
| 6-Br | 2-Br-C₆H₄— |
| 4-NO₂ | 2-Cl-C₆H₄— |
| 6-CF₃ | 2-CF₃-C₆H₄— |
| 6-CH₃ | 2-CH₃-C₆H₄— |
| 4-CH₃(CH₂)₃ | 2-Cl-C₆H₄— |
| 6-CF₃O | 2-CF₃O-C₆H₄— |
| 6-CH₃O | 2-CH₃O-C₆H₄— |
| 4-CH₃(CH₂)₃O | 2-Cl-C₆H₄— |
| H | 3-Cl-C₆H₄— |
| H | 4-Cl-C₆H₄— |
| H | 2-C₂H₅-C₆H₄— |
| H | 2-CH₂CH₂CH₃-C₆H₄— |
| H | 2-CH(CH₃)₂-C₆H₄— |
| 3-Cl | C₆H₅— |

TABLE X-continued
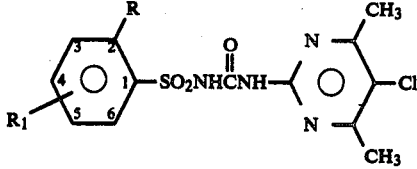
| R₁ | R |
|---|---|
| 4-Cl |  |
| 5-Cl |  |
| H | 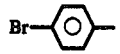 |
| H | 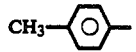 |
| H | 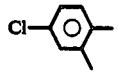 |
| H |  |
| H | 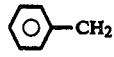 |
| H | 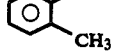 |
| H |  |
| 6-CH₃(CH₂)₂O | 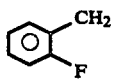 |
| H |  |
| H |  |
| H |  |
| H | 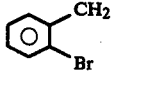 |
| H |  |
| H | 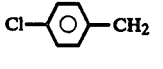 |
TABLE X-continued
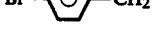
| R₁ | R |
|---|---|
| H | 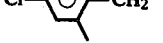 |
| H |  |
TABLE XI
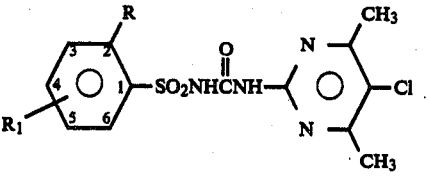
| R₁ | R |
|---|---|
| H |  |
| 6-F | 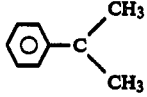 |
| 6-Cl | 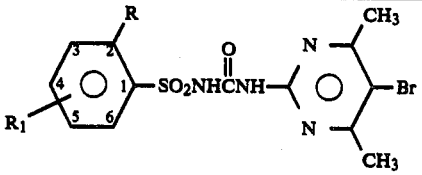 |
| 6-Br |  |
| 4-NO₂ |  |
| 6-CF₃ |  |
| 6-CH₃ |  |
| 4-CH₃(CH₂)₃ |  |
| 6-CF₃O | 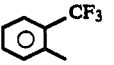 |
| 6-CH₃O |  |
| 4-CH₃(CH₂)₃O |  |

TABLE XI-continued

Structure: Benzene ring (positions 1-6) with R at position 2, R₁ at position 4/5, and $-SO_2NHC(O)NH-$ linked to a pyrimidine ring bearing 4,6-diCH₃ and 5-Br.

| R₁ | R |
|---|---|
| H | 2-chlorophenyl (Cl at ortho) |
| H | 4-chlorophenyl |
| H | 2-C₂H₅-phenyl |
| H | 2-CH₂CH₃-phenyl (n-propyl) |
| H | 2-CH(CH₃)₂-phenyl (isopropyl) |
| 3-Cl | phenyl |
| 4-Cl | phenyl |
| 5-Cl | phenyl |
| H | 4-Br-phenyl |
| H | 4-CH₃-phenyl |
| H | 2,4-diCl-phenyl |
| H | C₆H₅CH₂ (benzyl) |
| H | 2-CH₃-benzyl |
| H | 2-C₂H₅-benzyl |
| H | 2-F-benzyl |
| 6-CH₃(CH₂)₂O | 2-O(CH₂)₂CH₃-phenyl |
| H | 2-Cl-benzyl |
| H | 2-Br-benzyl |
| H | 4-CH₃-benzyl |
| H | 4-Cl-benzyl |
| H | 4-Br-benzyl |
| H | 3,4-diCl-benzyl |
| H | C₆H₅CH(CH₃) |
| H | C₆H₅C(CH₃)₂ |

TABLE XII

Structure: Benzene ring (positions 1-6) with R at position 2, R₁ substituent, linked via $-SO_2NHC(O)NH-$ to a pyrimidine bearing 4,6-diCH₃ and 5-CN.

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |

TABLE XII-continued

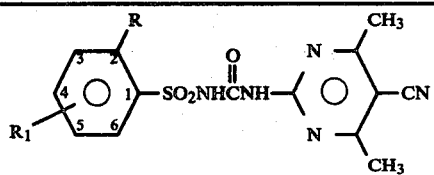

| R₁ | R |
|---|---|
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |
| H | 3-Cl-4-methyl-phenyl |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |
| 4-Cl | phenyl |
| 5-Cl | phenyl |
| H | 4-Br-phenyl |
| H | 4-CH₃-phenyl |
| H | 3,4-Cl₂-phenyl |

TABLE XII-continued

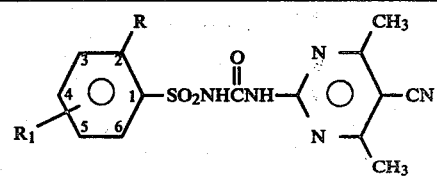

| R₁ | R |
|---|---|
| H | benzyl (C₆H₅-CH₂) |
| H | 2-CH₃-benzyl |
| H | 2-C₂H₅-benzyl |
| H | 2-F-benzyl |
| 6-CH₃(CH₂)₂O | 2-O(CH₂)₂CH₃-phenyl |
| H | 2-Cl-benzyl |
| H | 2-Br-benzyl |
| H | 4-CH₃-benzyl |
| H | 4-Cl-benzyl |
| H | 4-Br-benzyl |
| H | 3,4-Cl₂-benzyl |
| H | α-methylbenzyl (C₆H₅-CH(CH₃)) |
| H | α,α-dimethylbenzyl (C₆H₅-C(CH₃)₂) |

TABLE XIII

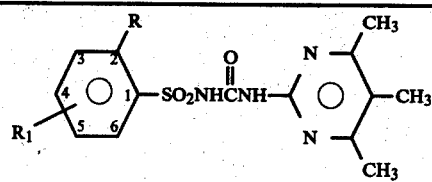

| R₁ | R |
|---|---|
| H | C₆H₅ |
| 6-F | 2-F-C₆H₄ |
| 6-Cl | 2-Cl-C₆H₄ |
| 6-Br | 2-Br-C₆H₄ |
| 4-NO₂ | 2-Cl-C₆H₄ |
| 6-CF₃ | 2-CF₃-C₆H₄ |
| 6-CH₃ | 2-CH₃-C₆H₄ |
| 4-CH₃(CH₂)₃ | 2-Cl-C₆H₄ |
| 6-CF₃O | 2-OCF₃-C₆H₄ |
| 6-CH₃O | 2-OCH₃-C₆H₄ |
| 4-CH₃(CH₂)₃O | 2-Cl-C₆H₄ |
| H | 3-Cl-4-CH₃-C₆H₃ (phenyl with Cl and CH₃) |
| H | 4-Cl-C₆H₄ |
| H | 2-C₂H₅-C₆H₄ |
| H | 2-CH₂CH₂CH₃-C₆H₄ |
| H | 2-CH(CH₃)₂-C₆H₄ |
| 3-Cl | C₆H₅ |

TABLE XIII-continued

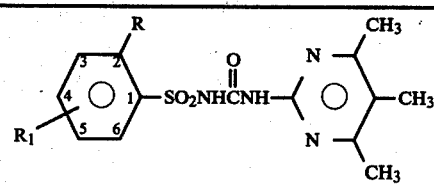

| R₁ | R |
|---|---|
| 4-Cl | C₆H₅ |
| 5-Cl | C₆H₅ |
| H | 4-Br-C₆H₄ |
| H | 4-CH₃-C₆H₄ |
| H | 3,4-Cl₂-C₆H₃ |
| H | C₆H₅—CH₂ |
| H | 2-CH₃-C₆H₄—CH₂ |
| H | 2-C₂H₅-C₆H₄—CH₂ |
| H | 2-F-C₆H₄—CH₂ |
| 6-CH₃(CH₂)₂O | 2-O(CH₂)₂CH₃-C₆H₄ |
| H | 2-Cl-C₆H₄—CH₂ |
| H | 2-Br-C₆H₄—CH₂ |
| H | 4-CH₃-C₆H₄—CH₂ |
| H | 4-Cl-C₆H₄—CH₂ |
| H | 4-Br-C₆H₄—CH₂ |
| H | 3,4-Cl₂-C₆H₃—CH₂ |

TABLE XIII-continued

Structure: Phenyl ring with R at position 2, R₁ at position 5, SO₂NHCNH(C=O) linker at position 1, attached to a pyrimidine ring with CH₃ at top, CH₃ middle, CH₃ bottom positions.

| R₁ | R |
|---|---|
| H | phenyl-CH(CH₃)- |
| H | phenyl-C(CH₃)₂- |

TABLE XIV

Structure: Phenyl ring with R at position 2, R₁ at position 5, SO₂NHCNH(C=O) linker at position 1, attached to a pyrimidine ring with CH₃ (top), CH₂CH₃ (middle), CH₃ (bottom) substituents.

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |

TABLE XIV-continued

| R₁ | R |
|---|---|
| H | 3-Cl, 5-CH₃-phenyl (Cl at one position, CH₃ at another) |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |
| 4-Cl | phenyl |
| 5-Cl | phenyl |
| H | 4-Br-phenyl |
| H | 4-CH₃-phenyl |
| H | 2,4-diCl-phenyl (Cl, Cl) |
| H | phenyl-CH₂- |
| H | 2-CH₃-phenyl-CH₂- |
| H | 2-C₂H₅-phenyl-CH₂- |
| H | 2-F-phenyl-CH₂- |
| 6-CH₃(CH₂)₂O | 2-O(CH₂)₂CH₃-phenyl |

4,378,991

TABLE XIV-continued

Structure: R-phenyl(positions 3,4,5,6,2,1)-SO2NHC(O)NH-pyrimidine with CH3, CH2CH3, CH3 substituents; R1 on phenyl

| R1 | R |
|---|---|
| H | 2-Cl-benzyl (C6H4(Cl)-CH2) |
| H | 2-Br-benzyl |
| H | 4-CH3-benzyl |
| H | 4-Cl-benzyl |
| H | 4-Br-benzyl |
| H | 3,4-diCl-benzyl |
| H | C6H5-CH(CH3)- |
| H | C6H5-C(CH3)2- |

TABLE XV

Structure: R-phenyl-SO2NHC(O)NH-pyrimidine with CH3, CH2CH2Cl, CH3 substituents; R1 on phenyl

| R1 | R |
|---|---|
| H | C6H5 |
| 6-F | 2-F-C6H4- |
| 6-Cl | 2-Cl-C6H4- |
| 6-Br | 2-Br-C6H4- |
| 4-NO2 | 2-Cl-C6H4- |

TABLE XV-continued

| R1 | R |
|---|---|
| 6-CF3 | 2-CF3-C6H4- |
| 6-CH3 | 2-CH3-C6H4- |
| 4-CH3(CH2)3 | 2-Cl-C6H4- |
| 6-CF3O | 2-OCF3-C6H4- |
| 6-CH3O | 2-OCH3-C6H4- |
| 4-CH3(CH2)3O | 2-Cl-C6H4- |
| H | 3-Cl-C6H4- |
| H | 4-Cl-C6H4- |
| H | 2-C2H5-C6H4- |
| H | 2-CH2CH2CH3-C6H4- |
| H | 2-CH(CH3)2-C6H4- |
| 3-Cl | C6H5 |
| 4-Cl | C6H5 |
| 5-Cl | C6H5 |
| H | 4-Br-C6H4- |
| H | 4-CH3-C6H4- |
| H | 3,4-diCl-C6H4- |

TABLE XV-continued

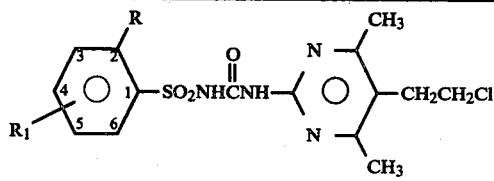

| R₁ | R |
|---|---|
| H | phenyl-CH₂ |
| H | 2-CH₃-phenyl-CH₂ |
| H | 2-C₂H₅-phenyl-CH₂ |
| H | 2-F-phenyl-CH₂ |
| 6-CH₃(CH₂)₂O | 2-CH₃-phenyl-O(CH₂)₂CH₃ |
| H | 2-Cl-phenyl-CH₂ |
| H | 2-Br-phenyl-CH₂ |
| H | 4-CH₃-phenyl-CH₂ |
| H | 4-Cl-phenyl-CH₂ |
| H | 4-Br-phenyl-CH₂ |
| H | 3,4-Cl₂-phenyl-CH₂ |
| H | phenyl-CH(CH₃) |
| H | phenyl-C(CH₃)₂ |

TABLE XVI

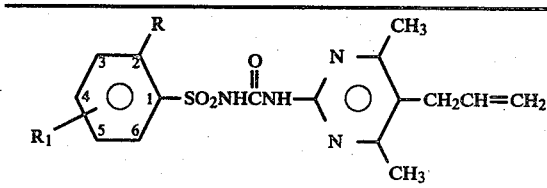

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |
| H | 2-Cl-6-CH₃-phenyl |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |

TABLE XVI-continued

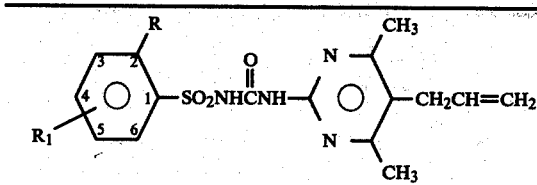

| $R_1$ | R |
|---|---|
| 4-Cl | phenyl |
| 5-Cl | phenyl |
| H | 4-Br-phenyl |
| H | 4-CH₃-phenyl |
| H | 2,3-di-Cl-phenyl |
| H | benzyl (C₆H₅CH₂) |
| H | 2-CH₃-benzyl |
| H | 2-C₂H₅-benzyl |
| H | 2-F-benzyl |
| 6-CH₃(CH₂)₂O | 2-CH₃-6-O(CH₂)₂CH₃-phenyl |
| H | 2-Cl-benzyl |
| H | 2-Br-benzyl |
| H | 4-CH₃-benzyl |
| H | 4-Cl-benzyl |
| H | 4-Br-benzyl |
| H | 2,4-di-Cl-benzyl |

TABLE XVI-continued

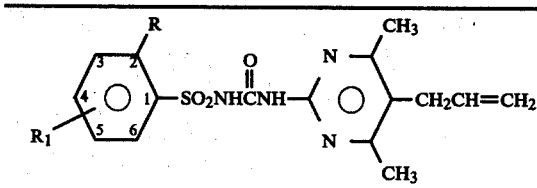

| $R_1$ | R |
|---|---|
| H | $C_6H_5$-CH(CH₃)– |
| H | $C_6H_5$-C(CH₃)₂– |

TABLE XVII

[structure with cyclopenta-fused pyrimidine]

| $R_1$ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |

TABLE XVII-continued

Structure: Ar(R)(R₁)-SO₂NHCNH-[cyclopenta-fused pyrimidine with N=C-N]

Phenyl ring numbered 1-6, R at position 2, R₁ at position 5.

| R₁ | R |
|---|---|
| H | 2-Cl-phenyl (3-Cl on ring shown) |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |
| 4-Cl | phenyl |
| 5-Cl | phenyl |
| H | 4-Br-phenyl |
| H | 4-CH₃-phenyl |
| H | 2,6-diCl-phenyl |
| H | phenyl-CH₂ (benzyl) |
| H | 2-CH₃-phenyl-CH₂ |
| H | 2-C₂H₅-phenyl-CH₂ |
| H | 2-F-phenyl-CH₂ |
| 6-CH₃(CH₂)₂O | 2-O(CH₂)₂CH₃-phenyl |

TABLE XVII-continued

| R₁ | R |
|---|---|
| H | 2-Cl-phenyl-CH₂ |
| H | 2-Br-phenyl-CH₂ |
| H | 4-CH₃-phenyl-CH₂ |
| H | 4-Cl-phenyl-CH₂ |
| H | 4-Br-phenyl-CH₂ |
| H | 3,4-diCl-phenyl-CH₂ |
| H | phenyl-CH(CH₃) |
| H | phenyl-C(CH₃)₂ |

TABLE XVIII

Structure: Ar(R)(R₁)-SO₂NHCNH-[4-methyl-cyclopenta-fused pyrimidine]

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |

TABLE XVIII-continued

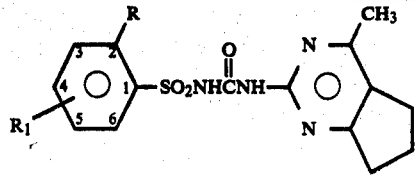

| $R_1$ | R |
|---|---|
| 6-CF$_3$ | 2-CF$_3$-phenyl |
| 6-CH$_3$ | 2-CH$_3$-phenyl |
| 4-CH$_3$(CH$_2$)$_3$ | 2-Cl-phenyl |
| 6-CF$_3$O | 2-OCF$_3$-phenyl |
| 6-CH$_3$O | 2-OCH$_3$-phenyl |
| 4-CH$_3$(CH$_2$)$_3$O | 2-Cl-phenyl |
| H | 3-Cl-phenyl |
| H | 4-Cl-phenyl |
| H | 2-C$_2$H$_5$-phenyl |
| H | 2-CH$_2$CH$_2$CH$_3$-phenyl |
| H | 2-CH(CH$_3$)$_2$-phenyl |
| 3-Cl | phenyl |
| 4-Cl | phenyl |
| 5-Cl | phenyl |
| H | 4-Br-phenyl |
| H | 4-CH$_3$-phenyl |
| H | 3,4-Cl$_2$-phenyl |

TABLE XVIII-continued

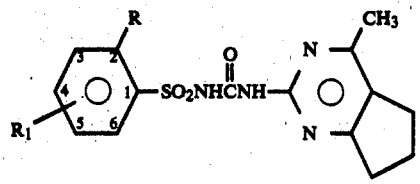

| $R_1$ | R |
|---|---|
| H | benzyl (PhCH$_2$) |
| H | 2-CH$_3$-benzyl |
| H | 2-C$_2$H$_5$-benzyl |
| H | 2-F-benzyl |
| 6-CH$_3$(CH$_2$)$_2$O | 2-O(CH$_2$)$_2$CH$_3$-phenyl |
| H | 2-Cl-benzyl |
| H | 2-Br-benzyl |
| H | 4-CH$_3$-benzyl |
| H | 4-Cl-benzyl |
| H | 4-Br-benzyl |
| H | 3,4-Cl$_2$-benzyl |
| H | α-methylbenzyl (PhCH(CH$_3$)) |
| H | α,α-dimethylbenzyl (PhC(CH$_3$)$_2$) |

TABLE XIX
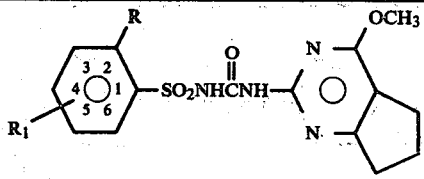
| R₁ | R |
|---|---|
| H |  |
| 6-F |  |
| 6-Cl |  |
| 6-Br |  |
| 4-NO₂ |  |
| 6-CF₃ |  |
| 6-CH₃ |  |
| 4-CH₃(CH₂)₃ |  |
| 6-CF₃O |  |
| 6-CH₃O |  |
| 4-CH₃(CH₂)₃O |  |
| H |  |
| H |  |
| H |  |
| H |  |
| H |  |
| 3-Cl |  |
TABLE XIX-continued
| R₁ | R |
|---|---|
| 4-Cl | 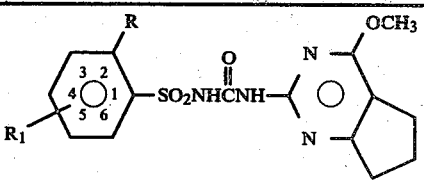 |
| 5-Cl |  |
| H |  |
| H |  |
| H |  |
| H |  |
| H |  |
| H |  |
| H |  |
| 6-CH₃(CH₂)₂O |  |
| H |  |
| H |  |
| H |  |
| H |  |
| H |  |
| H |  |
| H |  |

TABLE XIX-continued

[Structure: R-substituted phenyl-SO₂NHCNH-C(=O)-pyrimidine with OCH₃ and fused cyclopentane, positions 3,2,4,1,5,6 on phenyl with R₁]

| R₁ | R |
|---|---|
| H | phenyl-CH(CH₃) |
| H | phenyl-C(CH₃)₂ |

TABLE XX

[Structure: R-substituted phenyl-SO₂NHCNH-C(=O)-pyrimidine with Cl and fused cyclopentane, positions 3,2,4,1,5,6 on phenyl with R₁]

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |

TABLE XX-continued

| R₁ | R |
|---|---|
| H | 2-Cl-phenyl |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |
| 4-Cl | phenyl |
| 5-Cl | phenyl |
| H | 4-Br-phenyl |
| H | 4-CH₃-phenyl |
| H | 2,4-Cl₂-phenyl |
| H | phenyl-CH₂ |
| H | 2-CH₃-phenyl-CH₂ |
| H | 2-C₂H₅-phenyl-CH₂ |
| H | 2-F-phenyl-CH₂ |
| 6-CH₃(CH₂)₂O | 2-O(CH₂)₂CH₃-phenyl |

TABLE XX-continued
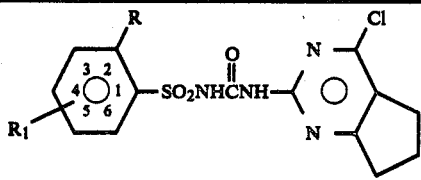
| R₁ | R |
|---|---|
| H |  |
| H |  |
| H | 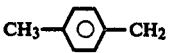 |
| H | 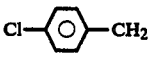 |
| H | 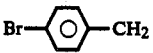 |
| H | 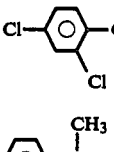 |
| H | 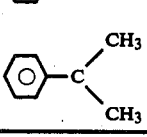 |
| H | 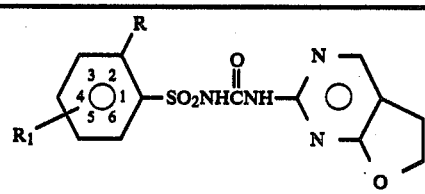 |
TABLE XXI
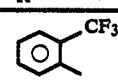
| R₁ | R |
|---|---|
| H | 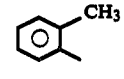 |
| 6-F | 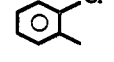 |
| 6-Cl | 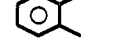 |
| 6-Br | 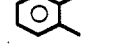 |
| 4-NO₂ | 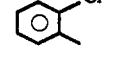 |
TABLE XXI-continued
| R₁ | R |
|---|---|
| 6-CF₃ | 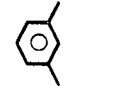 |
| 6-CH₃ | 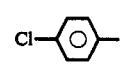 |
| 4-CH₃(CH₂)₃ | 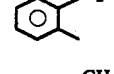 |
| 6-CF₃O | 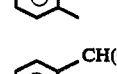 |
| 6-CH₃O | 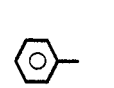 |
| 4-CH₃(CH₂)₃O | 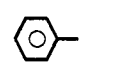 |
| H | 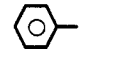 |
| H | 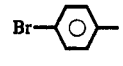 |
| H | 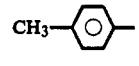 |
| H | 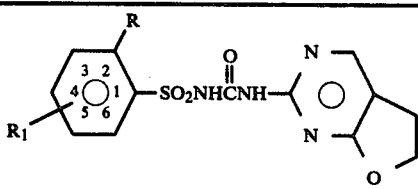 |
| H |  |
| 3-Cl |  |
| 4-Cl | |
| 5-Cl | |
| H |  |
| H |  |
| H |  |

TABLE XXI-continued

| R₁ | R |
|---|---|
| H | benzyl (C₆H₅-CH₂-) |
| H | 2-methylbenzyl |
| H | 2-ethylbenzyl |
| H | 2-fluorobenzyl |
| 6-CH₃(CH₂)₂O | 2-(O(CH₂)₂CH₃)-phenyl |
| H | 2-chlorobenzyl |
| H | 2-bromobenzyl |
| H | 4-methylbenzyl |
| H | 4-chlorobenzyl |
| H | 4-bromobenzyl |
| H | 3,4-dichlorobenzyl |
| H | α-methylbenzyl (C₆H₅-CH(CH₃)-) |
| H | α,α-dimethylbenzyl (C₆H₅-C(CH₃)₂-) |

TABLE XXII

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |
| H | 3-Cl-4-methyl-phenyl |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |

TABLE XXII-continued

Structure: R/R1-substituted phenyl-SO2NHCNH-pyrimidine with CH3, N, and fused tetrahydrofuran (O) ring

| R1 | R |
|---|---|
| 4-Cl | phenyl |
| 5-Cl | phenyl |
| H | 4-Br-phenyl |
| H | 4-CH3-phenyl |
| H | 3,4-di-Cl-phenyl |
| H | benzyl (phenyl-CH2) |
| H | 2-CH3-benzyl |
| H | 2-C2H5-benzyl |
| H | 2-F-benzyl |
| 6-CH3(CH2)2O | 2-O(CH2)2CH3-phenyl |
| H | 2-Cl-benzyl |
| H | 2-Br-benzyl |
| H | 4-CH3-benzyl |
| H | 4-Cl-benzyl |
| H | 4-Br-benzyl |
| H | 3-Cl-4-Cl-benzyl |
| H | α-methylbenzyl (CH3-CH-phenyl) |
| H | α,α-dimethylbenzyl (C(CH3)2-phenyl) |

TABLE XXIII

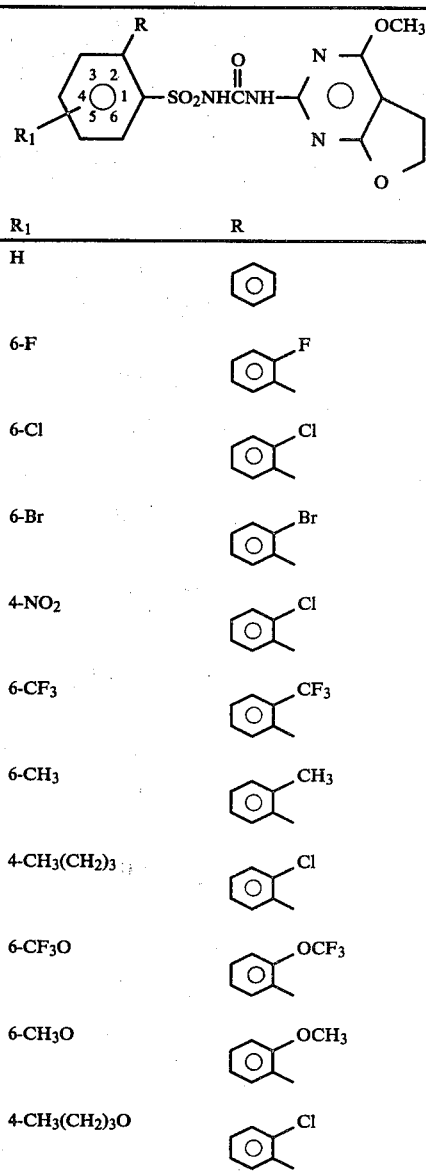

| R1 | R |
|---|---|
| H | phenyl |
| 6-F | 2-F-phenyl |
| 6-Cl | 2-Cl-phenyl |
| 6-Br | 2-Br-phenyl |
| 4-NO2 | 2-Cl-phenyl |
| 6-CF3 | 2-CF3-phenyl |
| 6-CH3 | 2-CH3-phenyl |
| 4-CH3(CH2)3 | 2-Cl-phenyl |
| 6-CF3O | 2-OCF3-phenyl |
| 6-CH3O | 2-OCH3-phenyl |
| 4-CH3(CH2)3O | 2-Cl-phenyl |

TABLE XXIII-continued

Structure: Ar(R,R₁)-SO₂NHCNH-pyrimidine with OCH₃, fused tetrahydrofuran ring

| R₁ | R |
|---|---|
| H | 3-chloro-2-methylphenyl (2-Cl) |
| H | 4-chloro-phenyl |
| H | 2-ethylphenyl (C₂H₅) |
| H | 2-(n-propyl)phenyl (CH₂CH₂CH₃) |
| H | 2-isopropylphenyl (CH(CH₃)₂) |
| 3-Cl | phenyl |
| 4-Cl | phenyl |
| 5-Cl | phenyl |
| H | 4-bromophenyl |
| H | 4-methylphenyl (CH₃) |
| H | 2,4-dichlorophenyl |
| H | benzyl (—CH₂—) |
| H | 2-methylbenzyl |
| H | 2-ethylbenzyl |
| H | 2-fluorobenzyl |
| 6-CH₃(CH₂)₃O | 2-(n-propoxy)phenyl O(CH₂)₂CH₃ |
| H | 2-chlorobenzyl |
| H | 2-bromobenzyl |
| H | 4-methylbenzyl |
| H | 4-chlorobenzyl |
| H | 4-bromobenzyl |
| H | 3,4-dichlorobenzyl |
| H | α-methylbenzyl (CH(CH₃)phenyl) |
| H | cumyl (C(CH₃)₂ phenyl) |

TABLE XXIV

Structure: Ar(R,R₁)-SO₂NHCNH-pyrimidine with Cl, fused tetrahydrofuran ring

| R₁ | R |
|---|---|
| H | phenyl |
| 6-F | 2-fluorophenyl |
| 6-Cl | 2-chlorophenyl |
| 6-Br | 2-bromophenyl |
| 4-NO₂ | 2-chlorophenyl |

TABLE XXIV-continued

[Structure: R-substituted phenyl-SO₂NHCNH-pyrimidine with Cl, N, N, O substituents]

| R₁ | R |
|---|---|
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |
| H | 3-Cl, 4-CH₃-phenyl |
| H | 4-Cl-phenyl (via methyl position) |
| H | 2-C₂H₅-phenyl |
| H | 2-CH₂CH₂CH₃-phenyl |
| H | 2-CH(CH₃)₂-phenyl |
| 3-Cl | phenyl |
| 4-Cl | phenyl |
| 5-Cl | phenyl |
| H | 4-Br-phenyl |
| H | 4-CH₃-phenyl |
| H | 3,4-diCl-phenyl |
| H | C₆H₅CH₂ (benzyl) |
| H | 2-CH₃-benzyl (CH₂) |
| H | 2-C₂H₅-benzyl (CH₂) |
| H | 2-F-benzyl (CH₂) |
| 6-CH₃(CH₂)₂O | 2-O(CH₂)₂CH₃-benzyl (CH₂) |
| H | 2-Cl-benzyl (CH₂) |
| H | 2-Br-benzyl (CH₂) |
| H | 4-CH₃-benzyl (CH₂) |
| H | 4-Cl-benzyl (CH₂) |
| H | 4-Br-benzyl (CH₂) |
| H | 3,4-diCl-benzyl (CH₂) |
| H | C₆H₅CH(CH₃) |
| H | C₆H₅C(CH₃)₂ |

TABLE XXV

Structure: R-substituted phenyl-SO₂NHCNH(=O)-pyrimidine with CH₂OCH₃ and CH₃ substituents on pyrimidine ring (positions 3,2,1 and 4,5,6 on phenyl)

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |
| H | 2-Cl-5-CH₃-phenyl (approx) |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |
| 4-Cl | phenyl-CH₂ (benzyl-like, phenyl) |
| 5-Cl | phenyl |
| H | 4-Br-phenyl |
| H | 4-CH₃-phenyl |
| H | 2,4-diCl-phenyl |
| H | benzyl (phenyl-CH₂) |
| H | 2-CH₃-benzyl |
| H | 2-C₂H₅-benzyl |
| H | 2-F-benzyl |
| 6-CH₃(CH₂)₂O | 2-O(CH₂)₂CH₃-phenyl |
| H | 2-Cl-benzyl |
| H | 2-Br-benzyl |
| H | 4-CH₃-benzyl |
| H | 4-Cl-benzyl |
| H | 4-Br-benzyl |
| H | 3,4-diCl-benzyl |

TABLE XXV-continued

Structure: phenyl ring with R (position 2) and R₁ (position 4), connected via SO₂NHCNH-C(=O) to a pyrimidine bearing CH₂OCH₃ and CH₃ substituents.

| R₁ | R |
|---|---|
| H | phenyl-CH(CH₃)- |
| H | phenyl-C(CH₃)₂- |

TABLE XXVI

Structure: R-substituted phenyl-SO₂NH-C(=O)-NH-(4-methylpyrimidin-2-yl), with R₁ on phenyl.

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |
| H | 3-Cl-phenyl (with methyl) |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |
| 4-Cl | phenyl |
| 5-Cl | phenyl |
| H | 4-Br-phenyl |
| H | 4-CH₃-phenyl |
| H | 3,5-diCl-phenyl |
| H | benzyl (phenyl-CH₂-) |
| H | 2-CH₃-benzyl |
| H | 2-C₂H₅-benzyl |
| H | 2-F-benzyl |
| 6-CH₃(CH₂)₂O | 2-O(CH₂)₂CH₃-phenyl |

TABLE XXVI-continued

Structure:
$$\text{Ar(R,R}_1\text{)-SO}_2\text{NH-C(=O)-NH-[pyrimidine with NH, N, CH}_3\text{, N]}$$

| R₁ | R |
|---|---|
| H | 2-ClC₆H₄-CH₂- |
| H | 2-BrC₆H₄-CH₂- |
| H | 4-CH₃-C₆H₄-CH₂- |
| H | 4-Cl-C₆H₄-CH₂- |
| H | 4-Br-C₆H₄-CH₂- |
| H | 3,4-Cl₂-C₆H₃-CH₂- |
| H | C₆H₅-CH(CH₃)- |
| H | C₆H₅-C(CH₃)₂- |

TABLE XXVII

Structure:
$$\text{Ar(R,R}_1\text{)-SO}_2\text{NH-C(=O)-NH-[pyrimidine with N, N, N, CH}_3\text{]}$$

| R₁ | R |
|---|---|
| H | C₆H₅- |
| 6-F | 2-F-C₆H₄- |
| 6-Cl | 2-Cl-C₆H₄- |
| 6-Br | 2-Br-C₆H₄- |
| 4-NO₂ | 2-Cl-C₆H₄- |
| 6-CF₃ | 2-CF₃-C₆H₄- |
| 6-CH₃ | 2-CH₃-C₆H₄- |
| 4-CH₃(CH₂)₃ | 2-Cl-C₆H₄- |
| 6-CF₃O | 2-OCF₃-C₆H₄- |
| 6-CH₃O | 2-OCH₃-C₆H₄- |
| 4-CH₃(CH₂)₃O | 2-Cl-C₆H₄- |
| H | 3-Cl-C₆H₄- (on methyl-bearing ring) |
| H | 4-Cl-C₆H₄- |
| H | 2-C₂H₅-C₆H₄- |
| H | 2-CH₂CH₂CH₃-C₆H₄- |
| H | 2-CH(CH₃)₂-C₆H₄- |
| 3-Cl | C₆H₅- |
| 4-Cl | C₆H₅- |
| 5-Cl | C₆H₅- |
| H | 4-Br-C₆H₄- |
| H | 4-CH₃-C₆H₄- |
| H | 3,4-Cl₂-C₆H₃- |

TABLE XXVII-continued

Structure: Ar(R,R₁)-SO₂NH-C(=O)-NH-[triazine with CH₃]

| R₁ | R |
|---|---|
| H | phenyl-CH₂ |
| H | 2-CH₃-phenyl-CH₂ |
| H | 2-C₂H₅-phenyl-CH₂ |
| H | 2-F-phenyl-CH₂ |
| 6-CH₃(CH₂)₂O | 2-CH₃-phenyl-O(CH₂)₂CH₃ |
| H | 2-Cl-phenyl-CH₂ |
| H | 2-Br-phenyl-CH₂ |
| H | 4-CH₃-phenyl-CH₂ |
| H | 4-Cl-phenyl-CH₂ |
| H | 4-Br-phenyl-CH₂ |
| H | 3,4-Cl₂-phenyl-CH₂ |
| H | phenyl-CH(CH₃) |
| H | phenyl-C(CH₃)₂ |

TABLE XXVIII

Structure: Ar(R,R₁)-SO₂NH-C(=O)-NH-[pyrimidine fused with tetrahydropyran-O ring]

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |
| H | 3-Cl-4-CH₃-phenyl |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |

TABLE XXVIII-continued

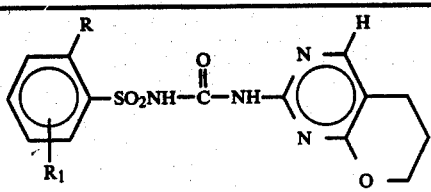

| R₁ | R |
|---|---|
| 4-Cl | phenyl |
| 5-Cl | phenyl |
| H | 4-Br-phenyl |
| H | 4-CH₃-phenyl |
| H | 2,5-diCl-phenyl |
| H | benzyl (C₆H₅-CH₂-) |
| H | 2-CH₃-benzyl |
| H | 2-C₂H₅-benzyl |
| H | 2-F-benzyl |
| 6-CH₃(CH₂)₂O | 2-O(CH₂)₂CH₃-phenyl |
| H | 2-Cl-benzyl |
| H | 2-Br-benzyl |
| H | 4-CH₃-benzyl |
| H | 4-Cl-benzyl |
| H | 4-Br-benzyl |
| H | 2,3-diCl-benzyl |

TABLE XXVIII-continued

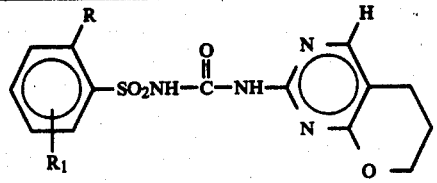

| R₁ | R |
|---|---|
| H | α-methylbenzyl (C₆H₅-CH(CH₃)-) |
| H | α,α-dimethylbenzyl (C₆H₅-C(CH₃)₂-) |

TABLE XXIX

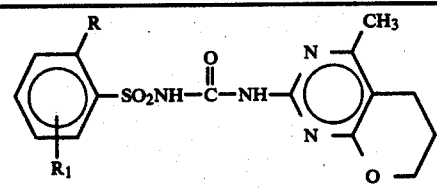

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |

TABLE XXIX-continued
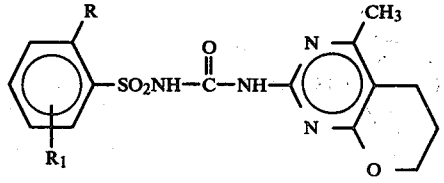
| R₁ | R |
|---|---|
| H |  |
| H | 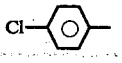 |
| H | 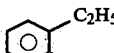 |
| H | 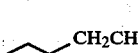 |
| H | 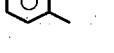 |
| 3-Cl | 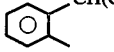 |
| 4-Cl |  |
| 5-Cl |  |
| H |  |
| H | 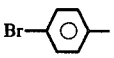 |
| H | 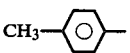 |
| H | 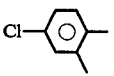 |
| H |  |
| H | 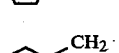 |
| H | 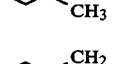 |
| 6-CH₃(CH₂)₂O | 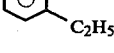 |
TABLE XXIX-continued
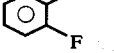
| R₁ | R |
|---|---|
| H | 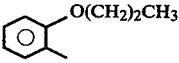 |
| H | 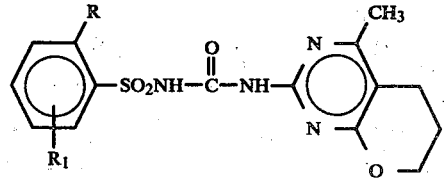 |
| H | 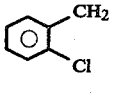 |
| H | 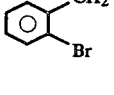 |
| H | 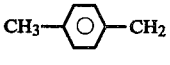 |
| H | 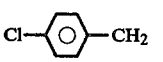 |
| H |  |
| H | 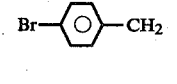 |
TABLE XXX
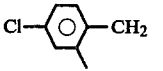
| R₁ | R |
|---|---|
| H | 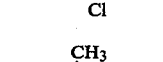 |
| 6-F | 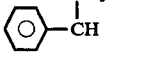 |
| 6-Cl | 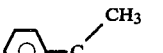 |
| 6-Br | 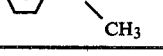 |
| 4-NO₂ |  |

TABLE XXX-continued structure: R-phenyl(R1)-SO2NH-C(=O)-NH-[pyrimidine with OCH3, fused with O-containing ring]

| R1 | R |
|---|---|
| 6-CF3 | 2-CF3-phenyl |
| 6-CH3 | 2-CH3-phenyl |
| 4-CH3(CH2)3 | 2-Cl-phenyl |
| 6-CF3O | 2-OCF3-phenyl |
| 6-CH3O | 2-OCH3-phenyl |
| 4-CH3(CH2)3O | 2-Cl-phenyl |
| H | 3-Cl-phenyl |
| H | 4-Cl-phenyl |
| H | 2-C2H5-phenyl |
| H | 2-CH2CH2CH3-phenyl |
| H | 2-CH(CH3)2-phenyl |
| 3-Cl | phenyl |
| 4-Cl | phenyl |
| 5-Cl | phenyl |
| H | 4-Br-phenyl |
| H | 4-CH3-phenyl |
| H | 3,4-diCl-phenyl |
| H | benzyl (phenyl-CH2) |
| H | 2-CH3-benzyl |
| H | 2-C2H5-benzyl |
| H | 2-F-benzyl |
| 6-CH3(CH2)2O | 2-O(CH2)2CH3-phenyl |
| H | 2-Cl-benzyl |
| H | 2-Br-benzyl |
| H | 4-CH3-benzyl |
| H | 4-Cl-benzyl |
| H | 4-Br-benzyl |
| H | 3,4-diCl-benzyl (with Cl at other position) |
| H | α-methylbenzyl (phenyl-CH(CH3)) |
| H | α,α-dimethylbenzyl (phenyl-C(CH3)2) |

TABLE XXXI

Structure: R-substituted phenyl-SO2NH-C(=O)-NH-[4-Cl-pyrimidine fused with oxygen-containing ring], where the phenyl bears R and R1 substituents.

| R1 | R |
|---|---|
| H | phenyl |
| 6-F | 2-F-phenyl |
| 6-Cl | 2-Cl-phenyl |
| 6-Br | 2-Br-phenyl |
| 4-NO2 | 2-Cl-phenyl |
| 6-CF3 | 2-CF3-phenyl |
| 6-CH3 | 2-CH3-phenyl |
| 4-CH3(CH2)3 | 2-Cl-phenyl |
| 6-CF3O | 2-OCF3-phenyl |
| 6-CH3O | 2-OCH3-phenyl |
| 4-CH3(CH2)3O | 2-Cl-phenyl |
| H | 3-Cl-2-methylphenyl |
| H | 4-Cl-phenyl |
| H | 2-C2H5-phenyl |
| H | 2-CH2CH2CH3-phenyl |
| H | 2-CH(CH3)2-phenyl |
| 3-Cl | phenyl |
| 4-Cl | phenyl |
| 5-Cl | phenyl |
| H | 4-Br-phenyl |
| H | 4-CH3-phenyl |
| H | 2,3-diCl-phenyl |
| H | benzyl (phenyl-CH2) |
| H | 2-CH3-benzyl |
| H | 2-C2H5-benzyl |
| H | 2-F-benzyl |
| 6-CH3(CH2)2O | 2-O(CH2)2CH3-phenyl |
| H | 2-Cl-benzyl |
| H | 2-Br-benzyl |
| H | 4-CH3-benzyl |
| H | 4-Cl-benzyl |
| H | 4-Br-benzyl |
| H | 3,4-diCl-benzyl |

TABLE XXXI-continued

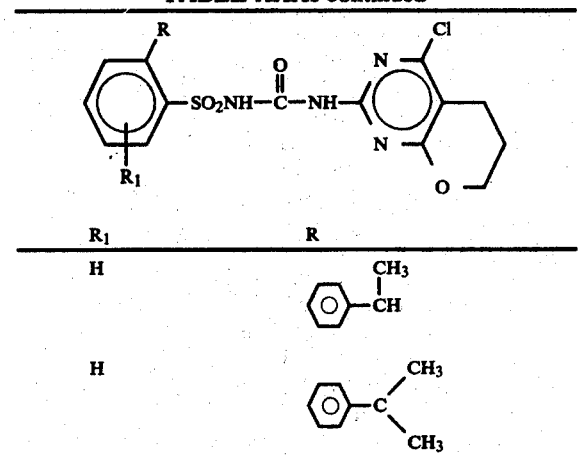

| R₁ | R |
|---|---|
| H | (phenyl)-CH-CH₃ |
| H | (phenyl)-C(CH₃)₂-CH₃ |

TABLE XXXII

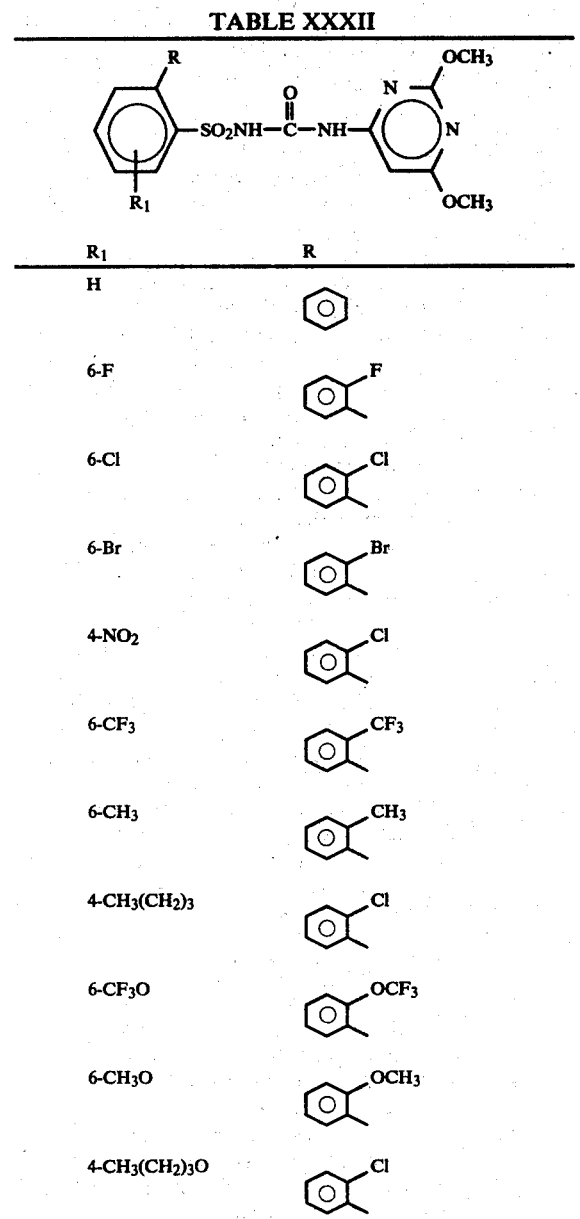

| R₁ | R |
|---|---|
| H | phenyl |
| 6-F | 2-F-phenyl |
| 6-Cl | 2-Cl-phenyl |
| 6-Br | 2-Br-phenyl |
| 4-NO₂ | 2-Cl-phenyl |
| 6-CF₃ | 2-CF₃-phenyl |
| 6-CH₃ | 2-CH₃-phenyl |
| 4-CH₃(CH₂)₃ | 2-Cl-phenyl |
| 6-CF₃O | 2-OCF₃-phenyl |
| 6-CH₃O | 2-OCH₃-phenyl |
| 4-CH₃(CH₂)₃O | 2-Cl-phenyl |

TABLE XXXII-continued

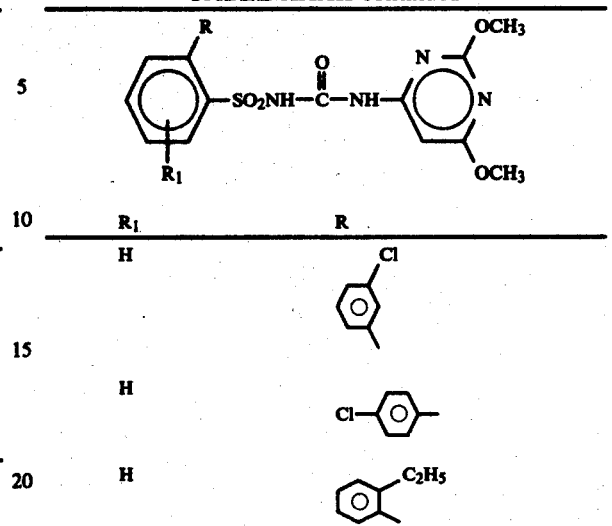

| R₁ | R |
|---|---|
| H | 2-Cl,5-CH₃-phenyl |
| H | 4-Cl-phenyl |
| H | 2-C₂H₅-phenyl |
| H | 2-CH₂CH₂CH₃-phenyl |
| H | 2-CH(CH₃)₂-phenyl |
| 3-Cl | phenyl |
| 4-Cl | phenyl |
| 5-Cl | phenyl |
| H | 4-Br-phenyl |
| H | 4-CH₃-phenyl |
| H | 2-Cl,3-Cl-phenyl |
| H | phenyl-CH₂ |
| H | 2-CH₃-phenyl-CH₂ |
| H | 2-C₂H₅-phenyl-CH₂ |
| H | 2-F-phenyl-CH₂ |
| 6-CH₃(CH₂)₂O | 2-O(CH₂)₂CH₃-phenyl |

TABLE XXXII-continued

Structure: R-substituted phenyl-SO$_2$NH-C(=O)-NH-(triazine with OCH$_3$, N, N, OCH$_3$), with R$_1$ on the phenyl ring.

| R$_1$ | R |
|---|---|
| H | 2-(chloromethyl)phenyl (–CH$_2$Cl ortho on benzene) |
| H | 2-(bromomethyl)phenyl (–CH$_2$Br ortho on benzene) |
| H | 4-methylbenzyl (CH$_3$–C$_6$H$_4$–CH$_2$–) |
| H | 4-chlorobenzyl (Cl–C$_6$H$_4$–CH$_2$–) |
| H | 4-bromobenzyl (Br–C$_6$H$_4$–CH$_2$–) |
| H | 3-chloro-4-chlorobenzyl (Cl–C$_6$H$_3$(Cl)–CH$_2$–) |
| H | α-methylbenzyl (C$_6$H$_5$–CH(CH$_3$)–) |
| H | α,α-dimethylbenzyl (C$_6$H$_5$–C(CH$_3$)$_2$–) |

EXAMPLE 1

3,2'-Dichloro-N-[(4-methoxy-6-methyl-1,3,5-triazin-2-yl)aminocarbonyl] [1,1'-biphenyl]-2-sulfonamide a. 3,2'-Dichloro-[1,1'-biphenyl]-2-sulfonyl chloride

To 588 ml of concentrated HCl and 196 ml of water at 0° to 10° was added, dropwise, 250 g of 2-chloroaniline. The mixture was purged with nitrogen and treated during a 1-hour period at 0° to 5° with a solution of 147 g of sodium nitrite in 294 ml of water. After 0.5 hour at 5° to 10° and 1.2 hour at 0° to 10°, the mixture was treated with 784 ml of cold (5° to 10°) concentrated HCl, then sparged with nitrogen for several minutes. Then, 55 ml of liquid SO$_2$ was added to the reaction mixture at 10°, followed by 15.4 g of anhydrous cupric chloride at 15° and the mixture was stirred slowly overnight. The heavy oil was drawn off, the aqueous layer extracted with butyl chloride and the combined organic portions washed with water (twice), half-saturated sodium bicarbonate solution (until the washings were basic) and saturated brine, then dried over MgSO$_4$, treated with activated carbon and filtered. The filtrate was evaporated to a deep-red oil and vacuum-distilled to remove material boiling up to 119° at 0.1 Torr. The pot residue was dissolved in butyl chloride, filtered through silica gel and the filtrate evaporated to provide an oil, which was vacuum-distilled. The fraction boiling at 180°–196°/(0.7–1.0 Torr) was chromatographed on a column of silica gel with butyl chloride/hexane 1:6 to 1:4 volume ratio) to provide, after evaporation of solvent, the sulfonyl chloride as an orange oil (Rf$\approx$0.58 on a silica gel-coated TLC plate with butyl chloride/hexane, 1:6 v/v, eluent); gas chromatography/mass spectral analysis indicates an approximate 95% purity. NMR confirmed the isomeric structure indicated.

b. 3,2'-Dichloro-[1,1'-biphenyl]-2-sulfonamide

A tetrahydrofuran (THF) solution of 1.57 g of the sulfonyl chloride (from a) was sparged with ammonia. The mixture was then diluted with water, the aqueous layer decanted, and the residual white solid filtered off and washed with butyl chloride. The solid was dissolved in hot ethyl acetate, the solution dried (MgSO$_4$) and diluted with hexane to precipitate the desired sulfonamide, 1.33 g (90% yield), m.p. 151°–153°.

c. 3,2'-Dichloro-[1,1'-biphenyl]-2-sulfonyl isocyanate

The sulfonamide (from b) was dissolved in 40 ml of thionyl chloride and refluxed for 42 hours. Evaporation of the unreacted thionyl chloride yielded the N-sulfinylsulfonamide as a yellow oil. The oil was contacted with 10 ml of a 13.8% phosgene solution in toluene, and a drop of pyridine, and was heated (under a dry-ice condenser) on a steam bath for 1.7 hours. The mixture was evaporated and the residue dissolved in acetonitrile and filtered. A sample of the acetonitrile solution was evaporated to a gum which was treated with a little methylene chloride and an infrared spectrum taken of the thus-thinned gum. The isocyanate presence was confirmed by the strong absorption peak at 2230 cm$^{-1}$.

d. 3,2'-Dichloro-N-[(4-methoxy-6-methyl-1,3,5-triazin-2-yl)aminocarbonyl] [1,1'-biphenyl]-2-sulfonamide The acetonitrile solution of the sulfonyl isocyanate (from c) was treated with 0.7 g of 2-amino-4-methoxy-6-methyl-s-triazine and the mixture stirred at ambient temperature for 18 hours. The white solid was filtered off and the filtrate evaporated to a tacky solid, which was the title sulfonylurea. This product was further purified by trituration with butyl chloride, dissolution in THF and precipitation from the THF solution by dilution with 0.5 N HCl. The solid was redissolved in THF. The butyl chloride solution obtained in the earlier trituration was evaporated, the residue dissolved in THF and precipitated by dilution of the THF solution with 0.5 N HCl; the precipitate was dried, boiled with butyl chloride; the butyl chloride mixture was then filtered and the filutrate diluted with hexane to precipitate a white solid. This solid was dissolved in THF, the solution combined with the THF solution obtained earlier and evaporated. The residue was washed with butyl chloride and hexane leaving the title sulfonylurea as 1.17 g of white solid, m.p. 141° (dec). The IR spectrum showed absorption at 1720 cm$^{-1}$ consistent with the urea carbonyl group.

EXAMPLE 2a 1,1'-Biphenyl-2-sulfonyl isocyanate

Into a dry, 500 ml, 3 neck round bottom flask, equipped with a dry-ice-cooled reflux condenser, stirrer, gas inlet tube and thermometer was charged 12 g of 1,1'-biphenyl-2-sulfonamide, 100 ml of xylene, 0.2 g of 1,4-diaza[2.2.2]bicyclooctane (DABCO) and 5 g of n-butyl isocyanate. The mixture was heated to 135° and then phosgene was passed into the system until the temperature dropped to 125°. Heating was continued to bring the mixture up to 135° and additional phosgene was added to lower the temperature to 120°. This cycling was repeated until the temperature of the refluxing mixture remained at 120° without further addition of phosgene. The mixture was then allowed to cool to room temperature, filtered and concentrated in vacuo. Any contact with moisture was scrupulously avoided due to the extreme reactivity of the sulfonyl isocyanate. The product thus obtained (yield 10.4 g) showed an absorption peak in the infrared spectrum at 2200 cm$^{-1}$, consistent with a sulfonyl isocyanate.

EXAMPLE 2b

N-[(4,6-Dimethylpyrimidin-2-yl)aminocarbonyl] [1,1'-biphenyl]-2-sulfonamide

To a suspension of 1.2 g of 2-amino-4,6-dimethylpyrimidine in 25 ml of acetonitrile was added 2.6 g of 1,1'-biphenyl-2-sulfonyl isocyanate with stirring at ambient temperature. After stirring for 2 hours, the mixture was filtered and the filtrate concentrated in vacuum. The residue thus obtained, after trituration with chlorobutane, melted at 78° with gas evolution. It showed peaks in the nuclear magnetic resonance spectrum (60 MHz) at $\delta$ 2.2, (singlet, CH$_3$); $\delta$ 6.56, (singlet, CH of pyrimidine) and at $\delta$ 6.8–7.9, (multiplet, phenyl hydrogens) in a ratio of 6:1:9, consistent with the desired structure.

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High-strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE XXXIII

| | Active* Ingredient | Diluent(s) | Surfactant(s) |
|---|---|---|---|
| Wettable Powders | 20–90 | 0–74 | 1–10 |
| Oil Suspensions, Emulsions, Solutions (including Emulsifiable Concentrates | 3–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High-Strength Compositions | 90–99 | 0–10 | 0–2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41.

R. W. Luckenbaugh, U.S. Pat. No. 3,309,192, Mar. 14, 1967, Col. 5, line 43 through Col. 1, line 62 and Examples 8, 12, 15, 39, 41, 52, 53, 58, 132, 138–140, 162–164, 166, 167 and 169–182.

H. Gysin and E. Knusli, U.S. Pat. No. 2,891,855, June 23, 1959, Col. 5, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 3

| Wettable Powder | |
|---|---|
| 3,2'-Dichloro-N—[(4-methoxy-6-methyl-1,3,5-triazin-2-yl)aminocarbonyl] [1,1'-biphenyl]-2-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 4

| Wettable Powder | |
|---|---|
| N—[(4,6-dimethoxypyrimidin-2-yl)aminocarbonyl] [1,1'-biphenyl]-2-sulfonamide | 50% |

| -continued | |
|---|---|
| Wettable Powder | |
| sodium akylnaphthalenesulfonate | 2% |
| low viscosity methyl cellulose | 2% |
| diatomaceous earth | 46% |

The ingredients are blended, coarsely hammer-milled and then air-milled to produce particles of active essentially all below 10 microns in diameter. The product is reblended before packaging.

EXAMPLE 5

| Granule | |
|---|---|
| wettable powder of Example 4 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 6

| Extruded Pellet | |
|---|---|
| N—[(4,6-Dimethylpyrimidin-2-yl)aminocarbonyl][1,1'-biphenyl]-2-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 7

| Oil Suspension | |
|---|---|
| 3,2'-Dichloro-N—[(4-methoxy-6-methyl-1,3,5-triazin-2-yl)aminocarbonyl] [1,1'-biphenyl]-2-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 8

| Wettable Powder | |
|---|---|
| N—[(4-methoxy-6-methylpyridin-2-yl)aminocarbonyl][1,1'-biphenyl]-2-sulfonamide | 20% |
| sodium alkylnaphthalenesulfonate | 4% |
| sodium ligninsulfonate | 4% |

| -continued | |
|---|---|
| Wettable Powder | |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 9

| Aqueous Suspension | |
|---|---|
| N—[(4,6-dimethyl-1,3,5-triazin-2-yl)aminocarbonyl][1,1'-biphenyl]-2-sulfonamide | 40.0% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| Water | 56.7% |

The ingredients are blended and ground together in a sand mill to produce particles essentially all under 5 microns in size.

EXAMPLE 10

| Low-Strength Granule | |
|---|---|
| N—[(4,6-dimethoxy-1,3,5-triazin-2-yl)aminocarbonyl][1,1'-biphenyl]-2-sulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 11

| Granule | |
|---|---|
| 3,2'-Dichloro-N—[(4-methoxy-6-methyl-1,3,5-triazin-2-yl)aminocarbonyl] [1,1'-biphenyl]-2-sulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water constant is reduced to the desired level, generally less than 1%. The material is then discharged, screened to the desired size range, generally 14–100 mesh (1410–149 microns), and packaged for use.

EXAMPLE 12

| High-Strength Concentrate | |
|---|---|
| N—[(4,6-dimethoxypyrimidin-2-yl)-aminocarbonyl] [1,1'-biphenyl]-2-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 13

| Wettable Powder | |
|---|---|
| 3,2'-Dichloro-N—[(4-methoxy-6-methyl-1,3,5-triazin-2-yl)aminocarbonyl] [1,1'-biphenyl]-2-sulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 14

| Wettable Powder | |
|---|---|
| N—[(4-methoxy-6-methyl-1,3,5-triazin-2-yl)aminocarbonyl] [1,1'-biphenyl]-2-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 15

| Dust | |
|---|---|
| N—[(4,6-dimethylpyrimidin-2-yl)-aminocarbonyl][1,1'-biphenyl]-2-sulfonamide | 10% |
| attapulgite | 10% |
| pyrophllite | 80% |

The active ingredient is blended with attapulgite and then passed through a hammer mill to produce particles substantially all below 200 microns. The ground concentrate is then blended with powdered pyrophllite until homogeneous.

EXAMPLE 16

| Solution | |
|---|---|
| N—[(4,6-dimethoxypyrimidin-2-yl)-aminocarbonyl][1,1'-biphenyl]-2-sulfonamide, sodium salt | 5% |
| water | 95% |

The salt is added directly to the water with stirring to produce the solution, which may then be packaged for use.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, oil well sites, drive-in theaters, around billboards, highway and railroad structures. By proper selection of rate and time of application, compounds of this invention may be used to modify plant growth beneficially, and also selectively control weeds in crops such as rice and wheat.

The precise amount of the compound of Formula I to be used in any given situation will vary according to the particular end result desired, the amount of foliage present, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.1 to 10 kg/ha. In general, the higher rates of application from within this range will be selected for adverse conditions or where extended persistence in soil is desired.

The compounds of Formula I may be combined with other herbicides and are particularly useful in combination with 3-(3,4-dichlorophenyl)-1,1-dimethylurea (diuron); the triazines such as 2-chloro-4-(ethylamino)-6-(isopropylamino)-s-triazine (atrazine); the uracils such as 5-bromo-3-sec-butyl-6-methyluracil (bromacil); N-(phosponomethyl)glycine (glyphosate); 3-cyclohexyl-1-methyl-6-dimethylamino-s-triazine-2,4(1H,3H)-dione (hexazinone); N,N-dimethyl-2,2-diphenylacetamide (diphenamide); 2,4-dichlorophenoxyacetic acid (2,4-D) (and closely related compounds); 4-chloro-2-butynyl 3-chlorophenylcarbamate (barban); S-(2,3-dichloroallyl)diisopropylthiocarbamate (diallate); S-(2,3,3-trichloroallyl)diisopropylthiocarbamate (triallate); 1,2-dimethyl-3,5-diphenyl-1H-pyrazolium methyl sulfate (difenzoquat methyl sulfate); methyl 2-[4-(2,4-dichlorophenoxy)phenoxy]propanoate (diclofop methyl); 4-amino-6-tert-butyl-3-(methylthio)-1,2,4-triazin-5(4H)one (metribuzin); 3-(3,4-dichlorophenyl)-1-methoxy-1-methylurea (linuron); 3-isopropyl-1H-2,1,3-benzothiodiazin-4(3H)-one-2,2-dioxide (bentazon); α,α,α-trifluoro-2,6-dinitro-N,N-dipropyl-p-toluidine (trifluralin); 1,1'-dimethyl-4,4'-bipyridinium ion (paraquat); monosodium methanearsonate (MSMA); 2-chloro-2',6'-diethyl(methoxymethyl)acetanilide (alachlor); 1,1-dimethyl-3-(α,α,α-trifluoro-m-tolyl)urea (fluometuron); N-(butoxymethyl)-2-chloro-N-(2,6-diethylphenyl)-acetamide (butachlor); 4-(2,4-dichlorophenxoy)-2-methoxy-1-nitrobenzene (chlormethoxynil); and S-[(4-chlorophenyl)methyl]diethylcarbamothioate (thiobencarb).

The activity of these compounds was discovered in greenhouse tests. The tests are described and the data resulting from them are shown below.

Test Procedure A

Seeds of crabgrass (Digitaria spp.), barnyardgrass (*Echinochloa crusgalli*), wild oats (*Avena fatua*), cassia (*Cassia tora*), morningglory (Ipomoea spp.), cocklebur (Xanthium spp.), sorghum, corn, soybean, rice, wheat and nutsedge tubers (*Cyperus rotundus*) were planted in a growth medium and treated pre-emergence with a G = growth retardation
H = formative effects
6Y = abscised flowers or buds.

TABLE A

[Structures: 2,6-dichlorophenyl-phenyl-SO$_2$NHC(O)NH-(4-methoxy-6-methyl-pyrimidin-2-yl) and phenyl-phenyl-SO$_2$NHC(O)NH-(4,6-dimethyl-pyrimidin-2-yl)]

| kg/ha | 0.1 | 0.4 | 2 |
|---|---|---|---|
| POST-EMERGENCE | | | |
| BUSHBEAN | 9C | 3C,3H | 3C,7G,6Y |
| COTTON | 6C,9G | 2C,2H,6G | 3C,4H,9G |
| MORNINGGLORY | 10C | 4C,9G | 3C,9G |
| COCKLEBUR | 4C,9G | 2C,3H,8G | 3C,9G |
| CASSIA | 3C,5G | 2C,7G | 2C,6G |
| NUTSEDGE | 5C,9G | 9G | 9G |
| CRABGRASS | 2C,6G | 5G | 5G |
| BARNYARDGRASS | 5C,8G | 3C,9H | 3C,9H |
| WILD OATS | 2C,8G | 1C,2G | 2C,9H |
| WHEAT | 2C,8G | 2H,6G | 2C,8G |
| CORN | 9C | 2C,8G | 2C,9H |
| SOYBEAN | 9C | 2C,8H | 2C,3H,9G |
| RICE | 5G | — | — |
| SORGHUM | 3C,9G | 2C,8H | 1C,9H |
| PRE-EMERGENCE | | | |
| MORNINGGLORY | 9G | 9G | 9G |
| COCKLEBUR | 9H | — | 9G |
| CASSIA | 1C | 9G | 9G |
| NUTSEDGE | 10E | 9G | 10E |
| CRABGRASS | 3G | 4G | 9H |
| BARNYARDGRASS | 9H | 2C,9H | 9H |
| WILD OATS | 6G | 8G | 8G |
| WHEAT | 7G | 7G | 8G |
| CORN | 1C,9G | 9H | 9G |
| SOYBEAN | 9H | 1C,6H | 9H |
| RICE | 5G | 9H | 9H |
| SORGHUM | 1C,9H | 2C,9H | 5C,9G | nonphytotoxic solvent solution of the compounds of Table IV. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including the cotyledonary ones), sorghum with four leaves, corn with four leaves, soybean with two cotyledondary leaves, rice with three leaves, wheat with one leaf, and nutsedge with three-five leaves were sprayed with a nonphytotoxic solvent solution of the compounds of Table IV. Other containers of the above mentioned weeds and crops were treated pre- or post-emergence with the same phytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment.

The following rating system was used:
0 = no effect
10 = maximum effect
C = chlorosis or necrosis
E = emergence inhibition

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*) and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B.

Note that certain compounds are useful as pre-emergence treatments for weed control in crops.

TABLE B
PRE-EMERGENCE ON FALLSINGTON SILT LOAM SOIL

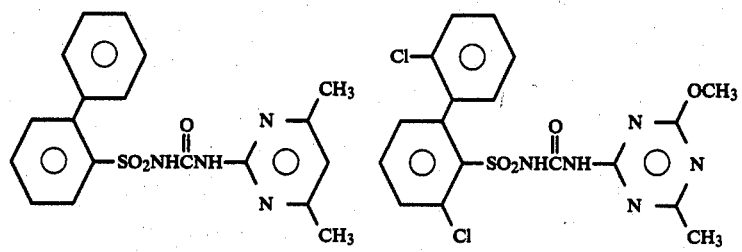

| Rate kg/ha | 0.06 | 0.25 | 0.06 | 0.25 |
|---|---|---|---|---|
| Crabgrass | 0 | 0 | 0 | 7C,8G |
| Barnyardgrass | 2G | 3C,4G | 3C,5G | 9C,9G |
| Sorghum | 2G | 3H,6G | 9C,9G | 9C,9G |
| Wild Oats | 0 | 0 | 4G | 4C,6G |
| Johnsongrass | 0 | 2G | 3G,6G | 8C,9G |
| Dallisgrass | 0 | 3G | 5G | 8G |
| Giant foxtail | 2C,3G | 3G | 5H,7G | 9C,9G |
| Ky. bluegrass | 6C,6G | 4C,6G | — | — |
| Cheatgrass | 3C | 3G | 6G | 10C |
| Sugarbeets | 0 | 3G | 3C,7G | 8C,9G |
| Corn | 0 | 2C,3G | 4G | 9C,9G |
| Mustard | 9C,9G | 3C,8G | 8C,8G | 9C,9G |
| Cocklebur | 0 | 0 | 5H,6G | 3H,6G |
| Pigweed | — | — | 0 | 5C,6G |
| Nutsedge | 0 | 5G | 7G | 9G |
| Cotton | 0 | 3G | 2G | 5G |
| Morningglory | 2G | 3G | 8G | 8G |
| Cassia | 0 | 0 | 0 | 2G |
| Teaweed | 0 | 5G | 3C,5G | 5G |
| Velvetleaf | 4G | 3H,4G | 3H,5G | 3H,5G |
| Jimsonweed | 0 | 3C,5G | 4G | 3C,4G |
| Soybean | 0 | 4G | 5H,5G | 5H,6G |
| Rice | 2C,3G | 2C,5G | 5G | 7G |
| Wheat | 0 | 2G | 3G | 6G |

Test C

Twenty-five cm diameter pots filled with Fallsington silt loam were planted to soybeans, cotton, alfalfa, corn, rice, wheat, sorghum, velvetleaf, (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a non-phytotoxic solvent. Fourteen days after treatment, all species were compared to untreated controls and visually rated for response to treatment. The rating system was as described previously for Test A. The data are presented in Table C. Several of the compounds tested by this procedure are useful for the post-emergence control of weeds in crops.

TABLE C

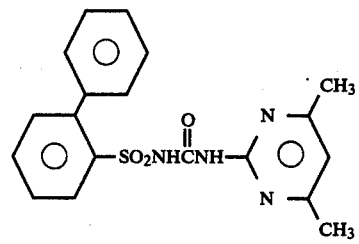

| Rate kg/ha | 0.06 | 0.25 |
|---|---|---|
| Soybeans | 2C,6G | 3C,8G |
| Velvetleaf | 1C,5G | 2C,8G |
| Sesbania | 1C,6G | 3C,8G |
| Cassia | 2G | 1C,3G |
| Cotton | 2C,3G | 3C,7G |
| Morningglory | 3C,9G | 6C,9G |
| Alfalfa | 0 | — |
| Jimsonweed | — | — |
| Cocklebur | 2C,5G | 3C,5G |
| Corn | 2G | 2G |
| Crabgrass | 1C,2G | 1C,2G |
| Rice | 2G | 3G |
| Nutsedge | 7G | 8G |
| Barnyardgrass | 1C,5G | 2C,6G |
| Wheat | 0 | 2G |
| Giant Foxtail | 5G | 1C,5G |
| Wild Oats | 1G | 2G |
| Sorghum | 1G | 3G |

Test D

Purple nutsedge (*Cyperus rotundus*) tubers were planted in 2 cm deep in Fallsington silt loam soil contained in 10 cm diameter plastic pots. Five tubers were planted in each pot. Compounds of this invention were dissolved in a non-phytotoxic diluent and sprayed at 560 l/ha in four methods of application: soil surface, tuber/soil, soil incorporated and post-emergence. The soil surface spray consisted of spraying the compound on the surface of the firmed covering soil. The tuber/soil spray consisted of spraying the compound on exposed tubers and subtending soil before adding the untreated covering soil. Soil incorporated treatment consisted in mixing the compound with the covering soil before using it to cover the tubers. The post-emergence treatment was sprayed on nutsedge foliage and the surrounding soil surface when nutsedge had emerged and grown to a height of about 12 cm. Pots receiving the post-emergence treatments were placed directly in the greenhouse. Pots receiving the other treatments were misted with about 0.3 cm water before being transferred to the greenhouse. Response ratings assessed after four weeks are recorded in Table D based on the same rating system as described in the procedure for Test A.

TABLE D

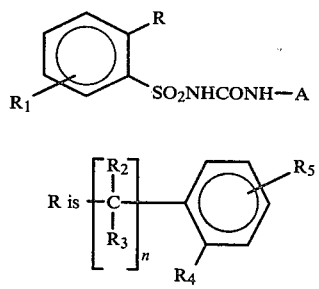

| Rate, kg/ha | Pre surface spray | Pre tuber & soil spray | Pre soil inc. 2.5 cm | Post foliar spray |
|---|---|---|---|---|
| 0.125 | 0 | 5G | 7G | 3G |
| 0.5 | 0 | 8E,9G | 9G | 5G |

What is claimed is:

1. A compound selected from

I

R<sub>1</sub>—⟨⟩—SO<sub>2</sub>NHCONH—A (with R on ring)

$n$ is 0 or 1;

$R_1$ is H, F, Cl, Br, $NO_2$, $CF_3$, $C_1$-$C_4$ alkyl, $OCF_3$ or $C_1$-$C_4$ alkoxy;

$R_2$ and $R_3$ are selected independently from H and $CH_3$;

$R_4$ is H, $C_1$-$C_3$ alkyl, F, Cl, Br, $CF_3$, $OCF_3$ or $C_1$-$C_3$ alkoxy;

$R_5$ is $CH_3$, Cl, Br or H;

A is

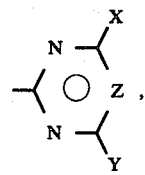

X is H, $CH_3$, $OCH_3$, $OCH_2CH_3$, $OCH_2CF_3$, $CH_2OCH_3$ or Cl;
Y is $CH_3$, $OCH_3$ or $OCH_2CH_3$;
Z is N, and
Q is $CH_2$ or O;
provided that the total number of carbons in R is less than or equal to nine.

2. A compound of claim 1 in which n is 0.

3. A compound of claim 2 in which A is

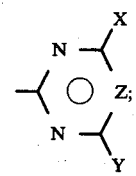

X is $CH_3$, $OCH_3$, $OCH_2CH_3$ or $CH_2OCH_3$;
Y is $CH_3$ or $OCH_3$; and
Z is N.

4. A compound of claim 3 in which $R_5$ is H, and $R_4$ is H or Cl.

5. A compound of claim 4 in which $R_1$ is H or Cl.

6. A compound of claim 1 which is 3,2'-dichloro-N-[(4-methoxy-6-methyl-1,3,5-triazin-2-yl)-aminocarbonyl][1,1'-biphenyl]-sulfonamide.

7. A compound of claim 1 which is N-[(4,6-dimethyl-1,3,5-triazin-2-yl)aminocarbonyl][1,1'-biphenyl]-2-sulfonamide.

8. A compound of claim 1 which is N-[(4,6-dimethoxy-1,3,5-triazin-2-yl)aminocarbonyl][1,1'-biphenyl]-2-sulfonamide.

9. A compound of claim 1 which is N-[(4-methoxy-6-methyl-1,3,5-triazin-2-yl)aminocarbonyl][1,1'-biphenyl]-2-sulfonamide.

10. A composition suitable for controlling the growth of undesired vegetation which comprises an effective amount of a compound of claim 1 and at least one of the following: surfactant, solid or liquid diluent.

11. A composition suitable for controlling the growth of undesired vegetation which comprises an effective amount of a compound of claim 2 and at least one of the following: surfactant, solid or liquid diluent.

12. A composition suitable for controlling the growth of undesired vegetation which comprises an effective amount of a compound of claim 3 and at least one of the following: surfactant, solid or liquid diluent.

13. A composition suitable for controlling the growth of undesired vegetation which comprises an effective amount of a compound of claim 4 and at least one of the following: surfactant, solid or liquid diluent.

14. A composition suitable for controlling the growth of undesired vegetation which comprises an effective amount of a compound of claim 5 and at least one of the following: surfactant, solid or liquid diluent.

15. A composition suitable for controlling the growth of undesired vegetation which comprises an effective amount of a compound of claim 6 and at least one of the following: surfactant, solid or liquid diluent.

16. A composition suitable for controlling the growth of undesired vegetation which comprises an effective amount of a compound of claim 7 and at least one of the following: surfactant, solid or liquid diluent.

17. A composition suitable for controlling the growth of undesired vegetation which comprises an effective amount of a compound of claim 11 and at least one of the following: surfactant, solid or liquid diluent.

18. A composition suitable for controlling the growth of undesired vegetation which comprises an effective amount of a compound of claim 12 and at least one of the following: surfactant, solid or liquid diluent.

19. A method for controlling the growth of undesired vegetation which comprises applying to the locus to be protected an effective amount of a compound of claim 1.

20. A method for controlling the growth of undesired vegetation which comprises applying to the locus to be protected an effective amount of a compound of claim 2.

21. A method for controlling the growth of undesired vegetation which comprises applying to the locus to be protected an effective amount of a compound of claim 3.

22. A method for controlling the growth of undesired vegetation which comprises applying to the locus to be protected an effective amount of a compound of claim 4.

23. A method for controlling the growth of undesired vegetation which comprises applying to the locus to be protected an effective amount of a compound of claim 5.

24. A method for controlling the growth of undesired vegetation which comprises applying to the locus to be protected an effective amount of a compound of claim 6.

25. A method for controlling the growth of undesired vegetation which comprises applying to the locus to be protected an effective amount of a compound of claim 7.

26. A method for controlling the growth of undesired vegetation which comprises applying to the locus to be protected an effective amount of a compound of claim 8.

27. A method for controlling the growth of undesired vegetation which comprises applying to the locus to be protected an effective amount of a compound of claim 9.

* * * * *